(12) United States Patent
Erbs et al.

(10) Patent No.: US 9,024,003 B2
(45) Date of Patent: *May 5, 2015

(54) AVIAN TELOMERASE REVERSE TRANSCRIPTASE

(75) Inventors: Philippe Erbs, Strasbourg (FR);
Jean-Marc Balloul, Strasbourg (FR);
Marina Kapfer, Schiltigheim (FR);
Nathalie Silvestre, Ergersheim (FR)

(73) Assignee: Transgene S.A., Illkirch (FR)

( * ) Notice: Subject to any disclaimer, the term of this patent is extended or adjusted under 35 U.S.C. 154(b) by 1004 days.

This patent is subject to a terminal disclaimer.

(21) Appl. No.: 12/159,930

(22) PCT Filed: Jan. 5, 2007

(86) PCT No.: PCT/EP2007/050120
§ 371 (c)(1),
(2), (4) Date: Mar. 23, 2009

(87) PCT Pub. No.: WO2007/077256
PCT Pub. Date: Jul. 12, 2007

(65) Prior Publication Data
US 2010/0173378 A1 Jul. 8, 2010

(30) Foreign Application Priority Data

Jan. 5, 2006 (EP) .................................. 06360001
Oct. 13, 2006 (EP) .................................. 06360047

(51) Int. Cl.
| | |
|---|---|
| C07H 21/04 | (2006.01) |
| C12N 15/52 | (2006.01) |
| C12N 15/85 | (2006.01) |
| C12N 9/12 | (2006.01) |

(52) U.S. Cl.
CPC .................................... *C12N 9/1276* (2013.01)

(58) Field of Classification Search
CPC .. C12N 5/0606; C12N 9/1048; C12N 9/1276; C12N 2510/00; C12N 2799/022; C12N 2502/13; C12Y 204/01087; A61K 35/12; A61K 48/00

USPC ........... 536/23.1, 23.2, 24.5; 435/320.1, 325, 435/349

See application file for complete search history.

(56) References Cited

FOREIGN PATENT DOCUMENTS

| | | |
|---|---|---|
| EP | 1 447 443 | 8/2004 |
| JP | 2002-300900 | 10/2002 |
| JP | 2004-000497 | 1/2004 |

OTHER PUBLICATIONS

McSharry et al., J Gen Virol. 2001, 82, 855-63.*
Michailidis et al Biochem Biophys Res Commun. 2005, 335 (1), 240-6.*
Bowie, et al. Science, 247: 1306-10, 1990.*
Skolnick et al. TIBTECH 18:34-39, 2000.*
Ivarie R Trends in Biotechnology, 2003 21(1): 14-19.*
Rychlik et al. Nuc. Acids Res. 18:6409-6412, 1990.*
Delaney et al. "The chicken telomerase reverse transcriptase (chTERT): molecular and cytogenetic characterization with a comparative analysis," *Gene*, vol. 339, pp. 61-69, (2004) Elsevier B.V.
Fragnet et al. "Virus et télomérase," Virologie, vol. 9, No. 6, pp. 443-455, (2005).
International Search Report for PCT/EP2007/050120 dated Jun. 8, 2007.
Written Opinion of the International Searching Authority dated Jun. 8, 2007.
English translation of the Japanese Office Action mailed Nov. 22, 2011, in corresponding Japanese Patent Application 2008-549016.
Gene ID: 101791475, TERT telomerase reverse transcriptase [*Anas platyrhyanchos* (mallard)], updated on Jan. 31, 2014, 2 pages.

* cited by examiner

*Primary Examiner* — Anoop Singh
(74) *Attorney, Agent, or Firm* — Buchanan Ingersoll & Rooney PC

(57) ABSTRACT

The present invention notably relates to novel recombinant telomerase reverse transcriptases, nucleic acid molecules coding them, cells comprising said nucleic acid molecule and use of these cells for the production of substance of interest.

15 Claims, 3 Drawing Sheets

SEQUENCE LISTING

```
<160> NUMBER OF SEQ ID NOS: 6

<210> SEQ ID NO 1
<211> LENGTH: 1304
<212> TYPE: PRT
<213> ORGANISM: Cairina moschata
```

<400> SEQUENCE: 1

```
Met Ala Gly Ala Glu Pro Phe Gly Ala Val Leu Gly Ala Leu Arg Asp
1               5                   10                  15

Cys Tyr Ala Gln Ala Ala Pro Leu Glu Thr Phe Leu Arg Gly Leu Gly
            20                  25                  30

Glu Ser Gly Ala Glu Ala Glu Val Val Arg Asp Asp Ala Ala
        35                  40                  45

Cys Tyr Arg Thr Phe Val Ser Gln Cys Val Val Cys Val Pro His Gly
        50                  55                  60

Ala Arg Asp Ile Pro Arg Pro Phe Ser Leu Glu Gln Leu Ser Ser Gln
65                  70                  75                  80

Ser Glu Val Ile Ser Arg Val Met Gln Arg Leu Cys Gly Lys Lys Lys
                85                  90                  95

Lys Asn Ile Leu Thr Tyr Gly Tyr Ser Leu Leu Asp Glu Asn Ser Ser
                100                 105                 110

His Phe Gln Ile Met Pro Leu Ser Asn Val Tyr Ser Tyr Leu Pro Asn
            115                 120                 125

Thr Ala Thr Glu Thr Met Arg Ile Ser Gly Leu Trp Glu Thr Leu Leu
130                 135                 140

Ser Arg Ile Gly Asp Asp Val Met Met Tyr Leu Leu Glu His Cys Ala
145                 150                 155                 160

Ile Phe Met Leu Val Pro Pro Ser Asn Cys Tyr Gln Val Cys Gly Gln
                165                 170                 175

Pro Ile Tyr Glu Leu Ile Ser Gln Asn Val Glu Ser Ala Pro Ala Phe
            180                 185                 190

Val Lys Gln Arg Leu Ser Lys His Lys Arg Ser Ser Leu Leu Lys Tyr
            195                 200                 205

Thr Gln Lys Arg Leu Thr Phe His Arg Gln Tyr Leu Ser Lys Ser Arg
210                 215                 220

Gln Ser Lys Arg Arg Gln Arg Leu Glu Ala Asn Val Ser Ser Met Arg
225                 230                 235                 240

Asn Lys Thr Ser Asn Asn Ile Gln Ser Leu Gly Ser Ala Ala Leu Glu
                245                 250                 255

Lys Gln Ser Ser Ser Asn Ala Gly Leu Ser Ala Thr Ala Pro Ser Leu
            260                 265                 270

Lys Arg Lys Leu Ala Arg Glu Gln Leu Glu Val Thr Ala Lys Arg Ala
            275                 280                 285

Arg Leu Glu Glu Lys Glu Arg Glu Glu Gln Ala Cys Asn Thr Ala Pro
290                 295                 300

Asn Val Asn Gln Ser Ile Pro Lys Arg Tyr Gly Thr Ser Cys Val Ala
305                 310                 315                 320

Ser Arg Ser Val Ser Leu Ile Lys Glu Lys Tyr Ile Ser Gln Arg Ser
                325                 330                 335

Asn Ser Asp Met Ser Arg Pro Leu Val His Asn Ser His His Gly
            340                 345                 350

Lys Lys Ser Val Ala Asp Lys Ser Ser Phe Leu Gln Gly Ala Glu Ser
            355                 360                 365

Asn Arg His Leu Lys Pro Ser Ile Glu Met Gln Ala Gly Ser Ser Arg
            370                 375                 380

Lys Arg Val Glu Ile His Arg Pro Ile Pro Arg Leu Asp Trp Ile Pro
385                 390                 395                 400

Ile Glu Pro Ala Glu Ser Ser Ser Ser Gly His Lys Lys Gln Glu Ser
```

-continued

```
                405                 410                 415
Pro Leu Ala His Leu Ala Glu Glu Leu Pro Asn Arg Val Leu Pro Ser
            420                 425                 430

Thr Ile Tyr Ile Asp Arg Lys Phe Leu Leu Tyr Ser Arg Arg Tyr Trp
            435                 440                 445

Gly Glu Arg Phe Pro Lys Ser Phe Leu Leu Asn Arg Leu Lys Gly Ser
    450                 455                 460

Glu Ala Gly Val Lys Arg Leu Ile Glu Thr Ile Phe Leu Ser Gln Asn
465                 470                 475                 480

Pro Phe Gly Gln Lys Arg Asn Gln Gly Leu Pro Gln Lys Lys Trp Arg
                485                 490                 495

Lys Lys Lys Leu Pro Lys Arg Phe Trp Arg Met Arg Ser Thr Phe Gln
            500                 505                 510

Lys Leu Leu Lys Asn His Gly Lys Phe Pro Tyr Val Ala Phe Leu Arg
            515                 520                 525

Gln Asn Cys Pro Leu Arg Ile Ser Glu Thr Ile Leu Gly Lys Ala Lys
            530                 535                 540

Leu Leu Ser Arg Ala Pro Leu Pro Gly Gln Ala Glu Ala His Lys Gln
545                 550                 555                 560

Ala Glu Gln Leu Gly Lys Glu Pro Ala Lys Arg Val Ala Ser Ser Arg
                565                 570                 575

Cys Glu Ser Gly His Thr Asn Val Pro Ser Ser Val Arg Ala Pro Leu
            580                 585                 590

Ala Ala Ser Ala Cys Val Glu Pro Gly Gly Glu Glu Gln Ile Pro Ala
            595                 600                 605

Glu Ala Ser Asp Ser Val Leu Arg Glu Leu Leu Lys Glu His Cys Ser
    610                 615                 620

His Phe Gln Val Tyr Leu Phe Val Arg Glu Cys Val Glu Arg Val Ile
625                 630                 635                 640

Pro Ala Glu Leu Trp Gly Ser Asn His Asn Lys Arg Arg Phe Phe Lys
                645                 650                 655

Asn Val Lys Ala Phe Ile Ser Met Gly Lys Tyr Ala Lys Leu Ser Leu
            660                 665                 670

Gln Val Leu Met Trp Lys Met Arg Val Asn Asp Cys Met Trp Leu Arg
            675                 680                 685

Leu Ala Lys Gly Asn His Phe Val Pro Ala Ser Glu His Arg Tyr Arg
            690                 695                 700

Glu Glu Ile Leu Ala Lys Phe Leu Tyr Trp Leu Met Asp Thr Tyr Val
705                 710                 715                 720

Val Glu Leu Leu Arg Ser Phe Tyr Ile Thr Glu Thr Met Phe Gln
                725                 730                 735

Lys Asn Met Leu Phe Tyr Tyr Arg Lys Cys Ile Trp Ala Lys Leu Gln
            740                 745                 750

Asp Ile Gly Ile Arg Lys His Phe Ala Lys Val Gln Leu Arg Pro Leu
            755                 760                 765

Thr Ala Glu Glu Met Glu Ala Ile His Gln Lys Lys Tyr Leu Pro Met
    770                 775                 780

Ala Ser Lys Leu Arg Phe Ile Pro Lys Val Ser Gly Leu Arg Pro Ile
785                 790                 795                 800

Val Arg Met Ser Gly Val Val Glu Ala Gln Thr Leu Ser Lys Glu Ser
                805                 810                 815

Arg Ala Lys Lys Met Asn His Tyr Asn Met Gln Leu Lys Asn Leu Phe
            820                 825                 830
```

-continued

Ser Val Leu Asn Tyr Glu Arg Thr Ile Asn Thr Ser Tyr Ile Gly Ser
        835                 840                 845

Ser Val Phe Gly Arg Asp Ile Tyr Lys Lys Trp Lys Thr Phe Val
850                 855                 860

Lys Lys Val Leu Lys Ser Asp Gly Glu Ile Pro His Phe Tyr Val
865                 870                 875                 880

Lys Ala Asp Val Ser Arg Ala Phe Asp Ser Ile Pro His Asp Lys Leu
                885                 890                 895

Val Glu Val Ile Ser Gln Val Leu Lys Pro Glu Lys Lys Thr Val Tyr
            900                 905                 910

Cys Ile Arg Arg Tyr Ala Val Val Met Ile Thr Gly Ser Gly Lys Thr
            915                 920                 925

Arg Lys Leu Tyr Arg Arg His Val Ser Thr Phe Lys Asp Phe Met Pro
        930                 935                 940

Asp Met Lys Gln Phe Val Ser Arg Leu His Glu Ser Thr Ser Leu Arg
945                 950                 955                 960

Asp Ala Ile Ile Val Glu Gln Ser Leu Thr Phe Asn Glu Thr Ser Ala
                965                 970                 975

Ser Leu Phe Asn Phe Phe Leu Gln Met Leu Asn Asn Asn Ile Leu Glu
            980                 985                 990

Ile Glu Arg Ser Tyr Tyr Leu Gln Cys Ser Gly Ile Pro Gln Gly Ser
            995                 1000                1005

Leu Leu Ser Thr Leu Leu Cys Ser Leu Cys Tyr Gly Asp Met Glu
1010                1015                1020

Asn Lys Leu Phe Ser Gly Val Gln Lys Asp Gly Val Leu Ile Arg
1025                1030                1035

Leu Ile Asp Asp Phe Leu Leu Val Thr Pro His Leu Thr His Ala
1040                1045                1050

Arg Thr Phe Leu Arg Thr Leu Ala Met Gly Ile Pro Glu Tyr Gly
1055                1060                1065

Phe Leu Ile Asn Pro Lys Lys Thr Val Val Asn Phe Ser Val Asp
1070                1075                1080

Asp Ile Pro Glu Cys Ser Glu Phe Lys Gln Leu Pro Asn Cys Arg
1085                1090                1095

Leu Ile Pro Trp Cys Gly Leu Leu Leu Asp Thr Gln Thr Leu Glu
1100                1105                1110

Val Tyr Cys Asp Tyr Ser Ser Tyr Ser Cys Thr Ser Ile Arg Ser
1115                1120                1125

Ser Leu Ser Phe Asn Ser Asn Arg Thr Ala Gly Lys Asn Met Lys
1130                1135                1140

His Lys Leu Val Ala Val Leu Lys Leu Lys Cys His Gly Leu Phe
1145                1150                1155

Leu Asp Leu Gln Ile Asn Ser Val Lys Thr Val Phe Ile Asn Val
1160                1165                1170

Tyr Lys Ile Phe Leu Leu Gln Ala Tyr Arg Phe His Ala Cys Val
1175                1180                1185

Ile Gln Leu Pro Phe Asn Gln Lys Val Arg Asn Asn Pro Asp Phe
1190                1195                1200

Phe Leu Arg Val Ile Ala Glu Asn Ala Ser Cys Cys Tyr Ser Met
1205                1210                1215

Leu Lys Ala Lys Asn Pro Gly Phe Thr Leu Gly Asn Arg Gly Ala
1220                1225                1230

| Ser | Gly | Met | Phe | Pro | Ser | Glu | Ala | Ala | Glu | Trp | Leu | Cys | Tyr | His |
|-----|-----|-----|-----|-----|-----|-----|-----|-----|-----|-----|-----|-----|-----|-----|
| 1235 |  |  |  |  | 1240 |  |  |  |  | 1245 |  |  |  |  |

| Ala | Phe | Thr | Val | Lys | Leu | Ser | Asn | His | Lys | Val | Val | Tyr | Lys | Cys |
|-----|-----|-----|-----|-----|-----|-----|-----|-----|-----|-----|-----|-----|-----|-----|
| 1250 |  |  |  |  | 1255 |  |  |  |  | 1260 |  |  |  |  |

| Leu | Leu | Lys | Pro | Leu | Lys | Phe | Cys | Met | Thr | Gln | Leu | Phe | Arg | Lys |
|-----|-----|-----|-----|-----|-----|-----|-----|-----|-----|-----|-----|-----|-----|-----|
| 1265 |  |  |  |  | 1270 |  |  |  |  | 1275 |  |  |  |  |

| Ile | Pro | Lys | Asp | Thr | Lys | Ala | Leu | Leu | Lys | Thr | Val | Thr | Glu | Pro |
|-----|-----|-----|-----|-----|-----|-----|-----|-----|-----|-----|-----|-----|-----|-----|
| 1280 |  |  |  |  | 1285 |  |  |  |  | 1290 |  |  |  |  |

| Ser | Ile | Cys | Gln | Asp | Phe | Lys | Ala | Ile | Leu | Asp |
|-----|-----|-----|-----|-----|-----|-----|-----|-----|-----|-----|
| 1295 |  |  |  |  | 1300 |  |  |  |  |  |

<210> SEQ ID NO 2
<211> LENGTH: 3915
<212> TYPE: DNA
<213> ORGANISM: Cairina moschata

<400> SEQUENCE: 2

| | | | | | |
|---|---|---|---|---|---|
| atggcgggcg | cggagccctt | cggcgccgtg | ctgggcgccc | tgcgggactg | ctacgcgcag | 60 |
| gcggccccgc | tggagacctt | cctccggggg | ctggggagag | gcggcgccga | ggaagccgag | 120 |
| gtggtgcggg | acgacgacgc | cgcctgctac | cgcaccttcg | tgtcccagtg | cgtggtgtgt | 180 |
| gtccccacg | gcgcccgcga | catccccgg | cccttcagct | tggagcagtt | atctagtcag | 240 |
| agcgaagtca | tctcaagagt | catgcagagg | ctgtgtggga | aaagaagaa | gaacatcctc | 300 |
| acatatggat | actccttgct | ggatgaaaac | agttctcact | tccaaatcat | gccgctctca | 360 |
| aacgtgtaca | gctacctgcc | caacaccgca | acagaaacca | tgcgtatcag | tggcctctgg | 420 |
| gaaacgctgc | tgagcaggat | aggggatgac | gtgatgatgt | atttattgga | gcactgtgca | 480 |
| atctttatgc | tggttccccc | tagtaactgt | taccaagtct | gtgggcaacc | aatttatgaa | 540 |
| cttatttcgc | aaaatgtaga | atcagcccca | gcgtttgtta | acaacggct | tcaaagcac | 600 |
| aaacgtagta | gcttgcttaa | gtatacgcag | aaaaggctaa | cgtttcacag | acagtatctt | 660 |
| tcaaagtcac | gtcagtcgaa | acgcaggcaa | agacttgaag | ctaatgtctc | cagcatgaga | 720 |
| aataaaacca | gcaataatat | acaaagccta | gggtccgctg | ctctggaaaa | acagagtagc | 780 |
| tccaatgcag | gtttgtcagc | tacagcacca | tccttaaaaa | ggaagcttgc | tagggaacaa | 840 |
| ctggaagtca | cggctaagag | agcaagatta | gaagagaaag | agagggagga | acaggcttgt | 900 |
| aatactgctc | ctaatgtaaa | ccagagtatt | cccaagaggt | atggaaccag | ctgtgtagca | 960 |
| tcacgttctg | taagtcttat | taaagaaaaa | tacatttctc | aaagaagtaa | cagtgatatg | 1020 |
| tctcgtcctt | ctttagttca | caattctcat | catgggaaga | agtctgtggc | agacaaaagc | 1080 |
| tctttcctgc | aaggagctga | gagtaacaga | catttaaagc | ccagcattga | aatgcaagca | 1140 |
| ggatccagca | ggaagagagt | agagatacac | aggcctatac | ctcggttgga | ttggatacca | 1200 |
| atcgaaccgg | cggaaagtag | ttcttcagga | cacaaaaagc | aggaaagtcc | cctagctcat | 1260 |
| ctggcagagg | agttaccaaa | tagggttttg | ccatctacaa | tatacattga | caggaagttt | 1320 |
| cttctgtatt | ctcgcaggta | ctgggggga | cgtttcccaa | aatccttcct | attgaatcgc | 1380 |
| ctgaagggta | gtgaggcagg | tgtaaagcga | ctaatagaaa | cgatattctt | aagccaaaat | 1440 |
| ccgtttgggc | aaaagcgcaa | ccaaggtctg | ccacagaaaa | aatggagaaa | gaagaagctt | 1500 |
| cccaaacgct | tctggagaat | gagaagtacg | tttcaaaaac | tcttaaagaa | tcatggaaag | 1560 |
| ttcccttacg | tagcttcttt | gagacaaaat | tgccctcttc | ggtatctga | accattttg | 1620 |
| ggaaaagcca | agctgctcag | tcgggcacct | ttgcctgggc | aagcagaggc | tcacaagcaa | 1680 |

```
gcagaacagc ttgggaagga gcctgctaag cgtgtggcaa gcagcagatg cgaatctggt    1740
cacaccaacg tgcccagcag cgtacgcgct cctctcgcag catctgcgtg cgtggagcca    1800
ggggggagg agcagatccc tgcagaggcg tctgattcag tcctcaggga gcttctcaag     1860
gagcactgca gccacttcca ggtgtacctc tttgtgaggg agtgcgtgga gcgggtgatc    1920
cccgccgagc tctggggttc aaaccataac aagcgccggt tcttcaagaa cgtgaaagca    1980
ttcatttcca tggggaagta cgctaagctt tccttgcagg tgttgatgtg aagatgaga     2040
gtaaatgact gcatgtggct tcgtctggcc aaaggtaatc actttgttcc tgcctctgaa    2100
caccgttacc gtgaagaaat tttggctaaa ttcctatact ggctgatgga tacgtatgtt    2160
gttgagttgc tcagatcatt tttctatatc accgagacca tgttccagaa aaatatgctt    2220
ttctactacc gaaagtgtat ttgggccaag ttacaggaca ttggaattag aaagcatttt    2280
gccaaagtac agctacgtcc tttaactgca gaggagatgg aagcgatcca tcagaaaaaa    2340
taccttccta tggcatcaaa gctccgtttc attcccaaag tcagtggact aagacccatc    2400
gtcagaatga gcggtgttgt tgaagcacaa acgttgagca aggaaagcag agcaaagaag    2460
atgaatcact acaacatgca actgaaaaat ctatttagtg tgttaaatta tgaacgaact    2520
ataaacacca gttacatcgg ctcttcagtg tttgggagag atgatatcta caagaagtgg    2580
aagacatttg ttaaaaaggt tcttaaatca gatggtgaaa ttcctcattt ctactatgta    2640
aaggccgatg tgtccagggc ttttgatagc attcctcacg ataaacttgt ggaagtgatt    2700
tcacaggtct aaaacctga gaaaaaaact gtctactgca tacggcgcta tgcagtggtt     2760
atgatcactg gaagtggaaa aaccaggaag ttatacagga acatgtttc tactttcaag    2820
gattttatgc cagacatgaa gcagtttgtg tcccggcttc atgagagtac ctcattgcga    2880
gatgcaataa tagttgaaca gagcttaact ttcaatgaga caagtgccag tctatttaat    2940
tttttcttc aaatgctaaa taataacatc ctggaaattg agcgcagcta ctacttacag     3000
tgctctggaa ttccacaggg ctcccttttg tcaaccttgc tttgcagctt gtgctatgga    3060
gacatggaaa acaaattatt cagtggggta cagaaggatg gagtcctgat ccgtctcatt    3120
gatgactttt tgcttgttac accacactta acgcatgcaa gaactttcct aaggactcta    3180
gcaatgggca ttcctgagta tggcttttg ataaacccca aaaagacggt ggtgaatttt      3240
tctgttgacg atatcccaga gtgttccgaa tttaaacagc tgccaaactg tcgtttgatc    3300
ccatggtgtg gcttattatt ggatacacag acacttgagg tttactgtga ttactccagc    3360
tattcctgta cttctatcag atcaagtctt tccttcaatt caaacagaac agctgggaaa    3420
aacatgaaac acaaattggt tgcagtcctt aaactgaaat gccatggctt gtttcttgat    3480
ttacagatca atagcgttaa aacagttttc attaatgtct acaagatatt tttacttcag    3540
gcttacaggt tccatgcctg tgttattcaa cttccattca accagaaagt taggaacaat    3600
cctgatttct tcctcagagt catcgctgag aatgcatcgt gctgctattc tatgctgaaa    3660
gctaaaaatc cagggtttac tttaggtaac agaggtgcat ctggcatgtt cccttctgag    3720
gcagcagagt ggctctgcta tcatgccttc actgtcaaac tgtcaaacca caagttgtt    3780
tacaaatgct tgcttaagcc cctgaagttc tgtatgacac agctattccg gaagatccca    3840
aaggatacta aggcactact gaagacagtg acagaaccat ctatttgtca agatttcaaa    3900
gctatcctgg actga                                                    3915
```

<210> SEQ ID NO 3
<211> LENGTH: 26916

<212> TYPE: DNA
<213> ORGANISM: Cairina moschata

<400> SEQUENCE: 3

```
gctatcactc catttcaagg aagggcaaaa ggccggttca ataccaacat ctgtgtagct    60
aagtaggatg aaatagatta ggtgaccaaa atatctgctt attcagcagg tgttgatcca   120
caggaggttc tacgataaag ctccagtagg agttgtacca gcgtaattcc tggagggcag   180
caataagtcc accatctaca ctccacaaag tctgatcttt aggtacaaag agctgtgctg   240
atctagaatg atgtggttag actgaatctg gctctaaatt tctgttatta gagtattatg   300
tattattaag taagaggcct tgcttcttac tgctgcctaa atgaagatta actttacagt   360
gaagcagagt gagagatgaa ggggtgataa tgtgtttgaa atatcagact taatctggca   420
ggtgataatc agttcattcc aaaaacgtta atgtgctgaa tcagattgac aagaaaatga   480
atcctaatta gttgaaatta atctgaagag aactgaaagt acatcatagc aaatagtaac   540
tcttcttcca catcacaagg aacagattcc actgtgttag tgatggaggt ttatacaaaa   600
aaaaaaaaaa aagaaaaacc agaacagctc ttaatttata tacttattga agcagattct   660
atatatgcat atgtatgcac attcattaat cagcagtaca tctcaacccct taaaagatcc   720
tggagaactg ttgcttgtca aaaagcactc aggttaggct aacatttgca gcttttgctc   780
tagcatacat ttacattagg tgtaaagaca aggaatgtgt aaaagagggt aaatgcattc   840
ctatctacaa tgttatgtat attttgttcc tgttatattg gctttacttc caaagttgta   900
gtttgcagta ttagtttctt tttattggta tccttgcata tatatatatt caataaatga   960
gttatgaatt tcatatttgc atatctgtcc tttttctgaa agtagaactt taaaactgac  1020
acttcagtgc ataaaagcag tgttccctat tgatgttaaa gtacctcgaa agtttttacca  1080
gaagacaagt gagtgcatac ttaaagtatg ctacttactt ggtggtaact gcgtatttgt  1140
gcattgttcc tgactttgtg taatgggtaa gttgctttgt atttaccact tgctaataat  1200
gtgaagtggc tggctcacta aaggttgcca ttctcacctt tcaaggactt cttgaaggct  1260
gtgtcataat aatttagagt aagacagata ctgagagcgc agagtgtaat atagttatgt  1320
tgcagaagag cggatagaca caggatgcat gttagaacca tataaatgtg gtgtaaaaga  1380
tcagcaaaac gaagaattgc ttggaagatg cttggttttg tccaaataaa agctgctga   1440
gagtgagaga gtgagtgagt aatattcagt attttttaaag tgtcgagaaa tgtaatgggg  1500
aaaaatttaa ataaatgtt ttttgtttgt tttaaaagga gctgtgtgct tttatgttga   1560
catgttgatt taattactgc ggtaggtatt tactgtgccc tgggaaacgg tatccccagt  1620
caacacagac ttatttgtca ggaaaaaaat tgtcatagat catcttcaaa taagagttga  1680
caaataatca atcttgatg gagtataatt attaatactg tgattacata tccatctttg  1740
caagggtttc ctgaaaaggt cagttttaag tcttctattg tcaaatctga tgtttggagt  1800
agttcgctac atggtgtttg atgccatgta aatagttacc agatagacgt tttattttat  1860
gtgctgtatg ttttttgtttt tcattcagtc agctggaatc attgaaacag agaaggtttc  1920
tcaagaaata tcctgaacct gttttgtgga tgtcttcatt gcaatagctg gtcactgaaa  1980
tcttggaata acgacagagg aatccatagg cacaggacca aacaccttc attgtcctca   2040
tatagcgtga tgttagggca gagtggtgag tacttcagtg gctcctgtgt ccatgcttta  2100
atgaactcta cttaatctac catatgtaag agacttgcag cacaggcaaa acaagggaag  2160
ttatctttgt gcctagataa tgtaccacat atggtaaaca attttcaagc ctcagagaca  2220
```

-continued

```
aaagaaggat gctgtaaagt ctcaagtctc agcttgtgtc tctgtttcca cctttctgtt    2280
ctttctgttc agacctctgg gccagtaatt taaactggaa aattaatgga acagagaaac    2340
tgtttgtgag cctatagaaa gatcaaattg tgtcagagta atgttgctcc ttctacaccc    2400
agataaactt tttgagcaga ggagaagcag tgaacagagc tttactttca tgactttgca    2460
taagaaaaca tgggaatgtg gtccgagacc aatttaaaaa tagaggtttt gaaaacttgt    2520
ttggaaaaca aaacttgctt ggaaaaccct attcagagct gtgaatcatt cacagacaac    2580
ctcttagggt tgtagccact catcagctga atatgattca acgatatgct gaaaaaaaaa    2640
aacacaaaca ttgttgtgga atgtatgaac aggaatgtag tctgtaagat gcgtgtcttg    2700
gtccttcttc tttaggtaat agtagaacac cttttctggga aaatggtatc cagctgttgt    2760
aggcactgca ctccatggaa aatgtgaaga agtggaaaat aatccagaga aaagcaatga    2820
gagggatgac aggataaaaa atgagccttg ctttaaggtg atgagagaaa agtgtttttc    2880
aaatctgtaa gagagccaca gagaagaaag aaagaaacag ttctcatcat tgcaggtagg    2940
acaagaaaaa taggtttaag ttgctgcagg aagcctttag cttagacatc agaatgggta    3000
attgtccttg acagtaggaa gaattaagct gtagcatgca cttcctggag aggtcgtgga    3060
atctcaggaa ttaggtttta aagggaatat ttgtaggcat cttttggggc tggtgcaatt    3120
gtaggttgga ggtgctgggg ataaggctaa tggaaatccc taccagccac tctaaggcct    3180
tctgcaagga gtcagaacca cttttcggaa gtaaaactct gtactggcag aggtcctgtg    3240
cttgacctta aggctcagag ccatgcattt ccgttttcat cttttcactt aaaatagcac    3300
ttgtggtagt aataacatgc tcttgcggag tggcacaggt ctgcatggtt atgaactttc    3360
tgtcaccacc cagcaaatgg cattttccac tcttctgttt cagattttcg ggagtacttc    3420
cttactccca aattcctgat tgaatacgac tgaaaacttc aacacgtttt tagtgcacga    3480
agtgtacttt atacaaatgt gtgggactat tgcacacaac ttactgattt tcttcactgt    3540
gtgcacatgt gctctgtgat gatacagagt ttggggtgac tgaactgtta cccagtcttt    3600
accgaattag ggcagcgatc ttaaaccttc atctgaactt tgctagaga tgatcttcta    3660 ttttgtttag acagggttct ctgcttgctt gcatttgttc taaaacgaca gtctggatga    3720
gaagaaacca accagggctg gcactgccct accttttatt ccctggatac tttacttggc    3780
acatcacttg gcacacatgc aatacccttt tttcaccccg gtacccaaag aaaagacgtg    3840
ctcctgcaca gactcagcca aattcctgcc tgccagtgga gggcgttaca gaggcttggg    3900
gcagagggag gaaactcact cccaaagcat atactaaaaa taggccaatg cattgcaaac    3960
agctttgctg tgagagcttc cttctggcat gtagccatgc agctgcctta tagttttgag    4020
cctagatacc tccaaaacaa aacaaaaagt cgctaaagtt aaatgcagcc agcagtgctt    4080
atagtcttga taatccctac agtgtatcaa ttttagtttc ttccagagtg caggtagttt    4140
actcaattta acttcaaatg tctgagttac accattgaca ccattgtcaa gactagtgct    4200
ggcaatccct gaagtctgcc aagttcaaag cagggaggag gcctttaaag ttgaaatact    4260
cgggtgacgt gtccaaaaag ttttcctgtg gctttcctgt ggagtaggaa ctgcagtagc    4320
taggttgcaa aaagttttta aactctccaa attgctgcta actaaacatc cttaaatcct    4380
gacatgagag tatgaaatga gaaagtcagt tccttgattt agactagctt gaaaagaata    4440
aactttttgc acaggactcc ctggacagtt gggctggata atagaagtga ttcattcagg    4500
tcttgatgcc tacaagtttc ttgggttttg ccatattttc cagtgatttg tgacatcatt    4560
tttgccctaa aataaatcgc atcatgtcct gccgtatgtt ttgactatga aaatggaggt    4620
```

```
ttcggtttga ataccaaact tcgttgttac ttctttcaga ggctgttgat aaaggaaaac    4680
gtgaagcttt tatgtaaatg atcatgattt ctcatttgca tcaagaatat tttccaaaat    4740
agtagttaaa tccctccaat gattttcagc tatgtcacat aaatcaccga aaacacggta    4800
attttgcacg ggtgtttttt ctcccttttt ttattgtcta atactcagct tatatttgag    4860
tcttctgtat ccaattacct gatttgtgtg gcaattaaac agaagatcag cgtcattgta    4920
cttcacattc ttttaaaact catcagtagt atgaccacac tagttggtct tgtaagtttg    4980
taatttaaga tgtgcctgga aggggttcaa agagacagga gcagtagtgt gtctcacttc    5040
cctttggaaa gcctttctga tactgtcaag caatatttac atcaaagggg aactgaattc    5100
tggtaaactt ttccagactc caagtaaacc gaacaacctg agatttagat aaaccttggt    5160
ggatttaaaa acttgatggt atcactgtct aagacttgtg ttagcccatc agatattgca    5220
gacgtatatt ttgaggaaag gctttcagtt aattgataaa attaagagca gagttttggc    5280
aaaaaaaacc gccatctctg tcagtactt catggcatct tgaatttctg cagttagagg    5340
tacaggtgct ctgttctgca attacccgt gctgttaatt aaaatgtact gtttgctaaa    5400
tatgattagt gtctggagcc aggtagcttg aaaaagcttc aagattattt cttttttacca    5460 ggaccatcaa gttttagcc ctccctttag aggaaggttc agaggaggtc ctatttaatc    5520
tgtcccagaa gaaaggctat ttctccccct agaatgggc ttggcagtcc ttttcagagc    5580
acttttcatc cttgtctcat agggattttt aaggacagat ttctgaaagg attttccacc    5640
gggtaaagcg ggatcctgaa tgggtgacag ataatacgta ggaattctgg cttcctactg    5700
ccaggttgtt tatcttgaga tcttaaaaat ggacttattt cccttttaa gtgtaaactg    5760 agttcttgag gcacctttc cactgaagta tctgactttg cccttactgc ccatctcagt    5820
cttgcacatt taacccaaat tcagatccag ggtgtggtgt tactcctaga acagctctta    5880
ctgtttgagg atctgaatga ctattttgcc agcttgtgcc atacaactcg agaggacctg    5940 caaagggag gggagtcctg atgggcagtt ccctcccagc ctggcatgcg cttcgtgtct    6000
ccgcttccct tataatctgc ccagaaaaga tttctgaaat acttgagcag ctgccacaat    6060
ctgcatggga ggcagcagcc ttggcatgtg agctctgcca cctgatgccc ggtctgtact    6120
gaggcagtgc cagctggatc tgcaagcctc agcgaataca gccttcgtca gcgagttctc    6180
tgatcagatt gctgccttgg agccttttgc tggtcttcct cagctcttct cctgttactc    6240
agatagcctt accacctcct ctcatcatct tttgagtttc tatcctcacg ttacagccag    6300
gtaagcccat ttacccatgc tgatatcaac aggttccaga ttttttaaaa acaatcctg    6360 tctggctcac agctagggag cctctagtga cacagctaag tccctgcag ccatttagaa    6420 atgtttctgg agggatgcag gtacgtcttg cactcaggtg cctaatgaaa gcagattgac    6480
ctgttcattc cttcgaaagc aactaagcaa agtggggaat cccatgtctc tgccccactt    6540
ctgtgttcct gacggcaaga cctcctgcca gcaccaaccg cctgtgtttg gagtcagcca    6600
gccttccgtt ctgactgaag ttgaaggtac agtacaaact gctggctaaa agaagctgct    6660
tgacttgctt ttttaggagg cttgtcttgt ggggaaaaaa aaaaaagta cagataaatt    6720 ctgctgattc cttctgagtc acccagcagc gatggcaaag ctaggagaaa aaatgggatc    6780
acagagggat tgatgaatgg acagtgagtg acctgaagat ctaactcaaa ggacgttact    6840
tcaagtgcaa gtgtcaacat ataaatgctg agttgttgtc tccaagtacc ccactgttgg    6900
ggtatcctgg ttaccaagca aggttttagt aagtctgttc gaaaagttac atacagctga    6960
```

```
cattcatgca ggccatgatt tgccaggcct gagctctgag gtattcctgg acggttagag    7020
aggataaaat aatttagaag tcaggaaacc actcagagac aaaccattat ttataaaatt    7080
attttgcctt ctaaaagatg tgcgttccag agaaatcaca acgttggctc caacctttt    7140 gcatcatcta gctagaaaat gtgcagcttc cagataccgc cagatcacct cccttgaccc    7200
tgccctggaa acatcaatgg ctcccatacc agtaagaaca aaactggtca tctactaaat    7260
ccgttgctga tctcagctaa ccaacttcct gtaatatcag caaatatttc tgcttttgta    7320
aatctgttct tccttccata atgggggtgcc agcaggaatg cttgggatcc agaaatgcgc    7380
tggttggcag gaagaacaaa gaaattgttc acccagaagg gcaaaaaagg actaatgctt    7440
tcgtccgctt gggagaagtt gcacagaact tatgccaaca acttttgcac gcaatcagaa    7500
agatgccgct ggatgttact tttaatagca gacgttaata tcagttatta attagaaatg    7560
tcttcagtaa ccagactaaa agcagatcct gaaacactcc tgtggttgaa cagtctcttg    7620
acagacactg cccactgtcc agtaatgtca ggcgctctct gaacttgaca gggcagctgc    7680
tgtttttccc agccttctgg aaataggcca gctctgacat gtttctgata ttagctgggt    7740
gtatttcatt ctgctgccct aggcagtttg ataaaggctc cttcctcctg ctccagagct    7800
aacccaccca aactgtagcc gagcacctcg ctgcaacaaa actgcactcg ctagggttct    7860
gcctgtttgc ttcattaaga tctgcttaaa ttgtttcgta caaaggaaca ctcaaactga    7920
tttctgagcc caaagtagca gtgctaggtg tacatcagga gttgtttggc atgaagaaac    7980
attgccatgg cactgtatga ataaagttat ttttaagaat cattatccct tccttgatac    8040 caagtctttta tgcggcagaa aatcaaactt ggtctccacc cttacagaaa gcagaggaat    8100
gctttcagct gatagttgct taagctagaa tataagaaac catgaatttc tgtgtgcact    8160
gcggcattgc ccttcattcc agacctacag aaaaaaacga cacttttgtt actatttttt    8220
tccttcccat atgagaccag gggagctacc caggcatttc cattcttata attttacctc    8280
aagatcaaat tttctccagg cagttaaagg cagctgcacc cggagacctc gctcagcctc    8340
cccttgcatc ccacggagct gcgtttagtg agaaacctcc cccgaggtga cgggctgcag    8400
gggacccctt cccacacgcg tccccgtccc ttttctcagt gcaaacgcag ccaccgcccc    8460
ttgaaccctc ctccgggctc tctcggttcg gcggaggcag gaggggggccg tgcccgccgc    8520 ccggagctc ctcacagggc ccgggccccg gggcggagcg ccgcggcca tgttgagggc    8580 ggggagcgcg gaaggcggcg ccggggccgc tgcggggcgc ggcgcctccc cgctccccgc    8640
cgctcctcgc cgcccgcagc cgcaacaccg gccccggccc cggcgggccg cgccatggcg    8700 accccagcc cctgcatcgt ggtgagtgcg ggcccggcgc tgcctcctcg gcctcccgct    8760
gggcccggcg tgcggtgaac ggggaggggg gaggcggctg cggggagccg gcgggggccg    8820
cccgtccccg tggggcgccc cgcgtggcgt ggagtcacct tgagggggctc gggctcccgc    8880 tgccctgcac ggccccgccc ggccccagcc gccctcctc ggctgccggc tcggtctcgc    8940
ctcctgcccg gtgtcctgcc atggggccgg cggggtgttg gcaatttcgg ggcgctgctt    9000
gggcggctcg cggttgggag agccgcgggt gctgcctcag aaggcgccca gaaataactt    9060
ccaccagaaa taacttccac caggcaccga cccggcgtgg cacaacttcc tattcctgtt    9120
gctcctcaca gcgcgctcgg gaggtcgtgc tccgtgtacc aaaacctgcg agctcagcac    9180
ccgaactggg atgccttttg gaggaagacc ccgctgaggg tgtattttc atcatcagtg    9240 tgctctgcta agaatccttt ttttttaat tattattttt tttaacccca gccccggggtg    9300 ccgtgagcgg tagcgtgaca cgcatgtggc gcctcgcggc ccacggccat gcctgccgtc    9360
```

-continued

```
aggctgtgcc cgcgcgcctg cctgtacttt ctcgctaaaa atccatctgt aaaacccacc    9420
gaacagcccg ctcagtacca aacgtagcct gcaaggctta gtggatgtgc tagatgtagt    9480
tatggggctg aaccgtagga aatttccgta gctgctgaga gggacccagc tcctgacacg    9540
cagcaggtca cgggctcggt gcctggcctg ctgcgagcag gggttgtgca ggggctgctg    9600
tggctgggag ggcaggcctg gctcccggcc aaaatcctca ttaccgcttg cgcaaccaaa    9660
aaacatgtaa acagctggct gatcacaggc aaggtaagtg cttccttggg cactgaaatg    9720
gaagcgtgat ctgcaccggc agcggagctg aggtggatgc ttaccatgcc tgccccgctg    9780
cattgccagc agcaggcttc agtgttcccc acaaacttct ttttacactg agcagccttc    9840
agctgcgtaa ccaacaagtg aagcgattca aaatatattg tcattttcaa gtggcagcgg    9900
ggctaaggtt cagggggaagt ttttcttgg tgcttttgga acaatatgcc ctgaaccaca    9960
gcagtggttg tataattacg tacataggca aaccccttgt cctaattaat acactcctgc   10020
taatgttgca agctgtttca tgtggaaaat ctgcccgtgc ggaacaggtt gctgaaacag   10080
ggctttaatt tctgattcta aagatcttga acctccactg tttccagatg gtggtcagag   10140
aaggcttgtt tcataggcac ataacttgtc ccgttaatat agctgtcttg tcttgtattg   10200
acagctggct tgtatgtttt gttgtgattc ggtgttgtgg agatttggaa gatgtccctg   10260
ttacaaggtc tgcttactta gttgcaaagg caggttttgc attacactgc tgaaatcaga   10320
gatgttgaaa agctgaaagc tgcttgatcc ttgtttattt atttattttt aaatgaaata   10380
agattatttg aggtgtagta aatttcatttt ccccgctctc caatgggggg aaatgttgtt   10440
agggcttgaa atcatttccc ctccacatcg tgctgagcga cagctcatgt agcatttcag   10500
acaactcttg tgaactgtgg gttgtgcaag cttccacttt gtgctctgtt cagaaggaaa   10560
ataaggtgat cccaactagt gtaatggatt tggtagttta ttgagtaaag caaaggattg   10620
gcagtttctc actacaggct ttctataaga cttttgtagaa atctcacctt atttccttt    10680 cagattgacg atgatgaaca aggttacgac ctggacttgt tctgcatacc taaacattat   10740
gcagatgatt tggaaaaagt ctatattcct catgggctca tcatggacag gtttgtttga   10800
cttcagacag tacactgctc cagctgattc catgacactg gaaaaaacaa tcttccagtg   10860
atagttttgc tgcctagtga ctgtctaaac agattacatt taattagaga ctaagaaata   10920
cacatgttaa ttaactctct cttgtttggc ttcaaagagt ttgtacattt gcagttacgc   10980
tattgtttgg aaatttgtca attctcaaag aaatttgtgg tacgtagcag tctgtgactt   11040
tctttacagt gtttctttga tgttttactt aaagtaatta gaacacatta cttgttgtgc   11100
tagttcaatc taaaaacagt tatagtctct caaacatctt taggatatta ataagagtag   11160
attattaatc acattatgat aagacttttt catgttcatg tggtagataa ctaacaccca   11220
attttcccct actgtctgcg aaagacatta gcctttgcaa ataccaatct gtcacttgtg   11280
gttgctgaaa tgtatgattt tctctggaag tttatctcg tgatgagaaa tgggtacatg    11340
aacctataag gtgttttgt tttacttttgt gtaagtaaag tggaggagtt gctggagaca   11400
cagaaccact gaagagcggt tctgagtaga tcttgtgaat aggaatgctt ctagattttg   11460
catggtgctg tttgatcaga ttattacagt atttataata aaatgttttt taactttaca   11520
ctgaaagacc ctatataggaa agcattgga caaagtacag gtcattaagt agctgatgta   11580
aagtttgtaa tggcaggcat tctctgagaa acctgctgtc agctgctata ctgtaaatac   11640
ataccatgct ttctgaatta aattgcaaga taaatttaga aacaatgatc actgaaaaac   11700
```

-continued

```
tgttcagtgt tctcttgctc tgctttattg gcattatatt ttgcagtcag acaaattta    11760 ttcagcaaaa cataacgcta tagttgataa tttgagagtt ttcttgctcc tcagttagtg    11820
agagctgttg tcttttttggt tgtgctgatt tattttgctc tctgcatgga agctgaacct   11880
atctttggaa gaagaaaaca cccttatgtc tcttatctga cagtaaaaca attcaggggtg   11940 ttcagatttg ctttggctga gtatgatgta tgaaaacaaa gaagtttggc agtgttactg    12000
ttagattaac cttggaacgc aaaactttgt tgaccaatag tgggttaaag tgactgaagc    12060
attaggcaaa tatttctgag caaaatatgc ttccgagttt gcatgtgttt gctgttgttg    12120
tttgcaatac aaaatactgc tgccatagta agcaaactaa atgtgttaca acagctaact    12180
ctcttttttt ttttttttgta taggacagag agactggcac gagaaattat gaagggcatg   12240
ggaggacatc acattgtagc tctctgtgta ctcaagggtg gctataaatt ttttgctgat    12300
ttattagact acatcaaagc actgaacaga aacagtgaca aatcaatccc catgactgta    12360
gacttcatta ggttgaagag ttactgtgta agtatctctg caataccatg caattttttct   12420 gtaaatttga ctaacttcaa attaacaaca gggatgattg agaattgcca acaaatgttg    12480
caaaagcttt gcctaagtac tgcctaaatt gtgctaattt tatacaaata gttaagacaa    12540 ttaagggaa aaaagcagtc acaagctaac ttgttctttg tctatcttat atgatctggt     12600
ttctttcaga ctttatctcc tcggcccagt aaaatccaga gcaaagagac cctttccatg    12660
tcctttactt cttaaacaat ttcctctctg cccctgtcc cacctctaaa actgtggttc    12720
tagaataata cagaggatag tcctacaaat cttattacaa aaacttaact ctaggaattt    12780
tcatgtggct tagacatcac tcaccagata ggaaaacttg aaaactgtga gcatggttat    12840
atttgggttc cctacctcat cttttgtttg gctcaactga acaatgaatg gaatgaattg    12900
catttggcca tgaggaaata ctagattcat aaaaacagat ttatggttag cggccactga    12960
atatggtgct acctttaaa gcctaggtct aggttgcctt ggctttatgc ttttggaaaa    13020
gaatttattt tcattttgca cacaagtatt taactttaca gggaaatgga gcatgaggta    13080
gtatgtaaga ttttttataag ggaagcatta gattacattg tgcaggtcaa aggaggaagc    13140
agatgtatgt tagtactgta tgcttcctga ctcagcaaca gcctagtcta tgttttcaa     13200 gacagtatttt gtgggtaatt tagatttttt ccataagatc acctgtagtg tggaaataat    13260 taagttttttt gatttcaatt tacggtgtca aaataaattg cttcttaagg tcatgctgtt    13320
agttctgtgt ctcgatgact gtgttttcca gtcagtagta taagctactt gtcatggttg    13380
tggagtagtg cctgctgcag tagaaaaaaa tagattacta agttggaaac tcaactgcat    13440
tgttcattta attaaaccag atataggggt acttgcagat ttaggttgga ctgtagaaga    13500
gcttcaaaaa tgcgctgctg ctgttgagcg atctgtaaaa atttcacctc gttgagtggc    13560
aaagctcaga ccagtcagag tttggccagg cctgtttgca gaaaagctgt gccagctccc   13620
aaggtgtgtg tgcagtgatg tcctgggggct acctggaaac caccgtcatg tctgcagagc   13680
gtgctgcagt gactcagctg cactctttaa agagaaggca aggccaggca gaaagggaca    13740
tgccagcctt tcgttacatc ttgcaagggg agagctgctt gacacacttt gtttctgctc    13800
cccacaaaag attcaggctc cctctaccag tccattcaac cacaaagcca ctacgtgccc    13860
acatacgctg tctgtaaaag ccacaacaga aaggtgaatg tctctattag aggataatat    13920
ttgaaagaat aggaaataac tcccacccttt tttggcgagg aaatttgtat tttctgcttt   13980
cttcaaggaa cacatccaat aactttggtt tatttaaaat ataaggacta cacccttctg    14040
ctctctccac cttccgagta acttggaaca agctatggga taagtgttgt gaaacacctg    14100
```

```
gaaaaaatac tacattgcaa agcaaggctt attgtacagc atgtttttat tgttcatctt    14160
tatgcattag gcatgtattg gttctgctgc ttttattttt tacaccgccc ccccaaacta    14220
tagtgctttt atattaatag gaaactgaac agcaaaataa ttacggaagt tttaattctc    14280
tttttgtagt aagaaggagt aaacaaagag aaaagcagag aaatttacac agaaaggagt    14340
gtaagcagaa tgttttccat gaggtgttgg cttcagggtt ttggttttgt cagccaattc    14400
tgtaaaggaa tgttttcttg ttctatatga ccgaggagct ccagttactt gatgccccca    14460
ctagcagatt attacgagca tttcatttct gtcaactctc taaggtagtt attaatatcc    14520
agacttacgt tctttagatt gcataacttg atagactggg taagactgtc ctaacacaaa    14580
catgcgtgta attgattcac ttagtttttc cattattaatg gtgctggaat gttaaatctg    14640
ctctgtagtt ttcattcgtg ctttactaaa cggaggagtc agcattctta atgatgggaa    14700
aaccatcaca aaccgtaatg gacagttgaa agtagagcta gctctcttgt gattgttgtt    14760
ggatgcaatt actagatcac gctgcctgcc tttacagact gggtgaaaga tgttaaaaat    14820
accgtcgttg cataaacaaa gcagctgaac tcgtataatg gttctaaaat tgatgcgatt    14880
gatgttctat tcctatttga aattgatcat ttaatatttt caagcttatg ggttatttgt    14940
ttcataatgc aaagttcata ctatgattgc acccaaaaat aattctctaa gaatactgag    15000
atgatgaagc tgtgattaaa tgttgcttat aattcctgct ttcggagtcc ttacaaatga    15060
gttttaatga tctggcaagc tgttaagaaa ttgaaagata tgtttgtga acagaaccag    15120 atctctgtat tcttgacaaa tagtttattt tccttgtgct agaagaatgg cttttcacca    15180
gtttcctgca tgtaaagtta gagttaagca aaagttgctt atgtagtcac aaagggcagc    15240
caaaacacaa tggacgtgtt gcattgtcac tcagggaaat agggcttttc ggaggagtac    15300
tgcagcttta aggcaaaatc tagttaggct ggttgagaca gtattctgaa agatctcatg    15360
ttaactgagc cttatagcaa ataccatgag gaacttaaaa tgccttgtca ggggttacga    15420
tcttgcagca tgttattatt ttccagcaat gacaatgagg cagtgaaaac agatctaaac    15480
agtaaatctc taatgtgtta aatcacaaag cattaaagtc ttaccagtac tgaaatcaga    15540
aataatgctc ctgaagataa ttaaagtgtt gcttaattat taaacaaagt tctttccaat    15600
ggaaatctgg ttaaaaccag tgttggaaat ttgttaacca ttttgatcc tttaattgct    15660 cagaaactca gtacctgcat aggcgtgtag gtttatatgc cagcgaaggt ttatgttttg    15720
tgttaaaaaa tgtagcaatt tgcagggtgc ttggtgggaa gaagaagggc agattttgtt    15780
ggttagattg ttttctctg ctgatcagtg tacttgagta tgcataaccc acagggttct    15840
gtagtgatct gtagttctgt gttgttattg tttgattata gtgtgttgct ttgtagccag    15900
agagatcacc aggaaactga tctgcatgca tgtactgaga ggactggtct atcatctgtg    15960
catggtgttt taatggaaca aatatctgta acatctttct ccatcttcct tctgtaagaa    16020
atggtgcttt ttcatccctt ccatggaaaa aggacgaaat tcttattagt gtaggaatag    16080
ataagagaga atcctgcaac ataaacaggg aaaagcttaa agctgtcatt taagataatt    16140
ttaagatatg atgaacgcag gaaatgcccc tcagcattac aaaacgggtg cttaactgaa    16200
tcccattttc gtgattaatc taaccagtat ctctggcatt cagtagcagt ctgctgttta    16260
ctgggtcaag cagcagacat tttggacatc ctattttttgg acttttcaa cacagtggta    16320 ttggttctgt tcactatagt tttctttaaa acatggggta aaactgtaaa ggcgcttttt    16380
ctaatgtgtt gtgcttgcct ttttttaat gttttgtcat gggaatctaa aatagaaagt    16440
```

```
atctgttagt ctcgttatct gcttttacat acctagagct gtcagcactt ctttatccta   16500
gagcattgac gtcactgtcc aagggatttt aatacatttt ctctttactg taatcccagt   16560
gtcacttatg gtgtgctcag tgtgtgtttc tctctaaacc atttacccct tttttgcatg   16620
tgataacact tctactttt gtctgcaact ggtacagtat gaatatgtgt gtcagtgaaa   16680
acaggaagct gtatgtggcc gtctgttccc ctgtggtctc ctctctattg tatctgccat   16740
tttggggcgt ggggaaggaa ctgctctttt gctgcttgtc tgcatggtca tgcagtaagg   16800
ttgggcttca gactgaagcg gcaaaataat aaaggttttc taaagggaag atatgaagtg   16860
aagagctgtg agaatgaagt ttgaaaagtg gtatgaccct tcaaataaat gattaaattg   16920
taggataatg acatcatctg taagtagcac agtaatgagt atagcacaat taataagaac   16980
taggagacaa tgtcaaggtt taaagtcagc tgaatgactt taaataaact gcagagatct   17040
ggaggtaccc caggagttgt ttttaacttt cttatataac aaacagttca ctgatgctta   17100
catcaaagcc tagttttact aaagcaaaat gctgtacttc agtgatagga ttgtgtagct   17160
gtgtcgctgt ttaattacca caatgagtaa tttatcacta tttgtaaaat aggcaaaccc   17220
aagcttttct ggctattctt gtagcttata tttcttgttc ttaatctgtg ccttgtttgc   17280
tggctatttc attgttgtta tgattgctta tttttattca gagtaaggct ttctaaggca   17340
tcaaagttta aaatgtaaat taccagctat atagcagcgt acagcttgga aactttttt   17400
ttttcctgtt ttccatacct ttaatgaata tgtaggaaat aatatttttt taatatacat   17460
gtgtgtatat ataatggtga cagatgagaa gtggtgcctg tatttatgta aatatttttt   17520
caaacaatct tttatctgaa ataccatctt tcagtttgat tacttgtaat ttcttagtta   17580
atagatgttg ctggtgcaat gcttctgaaa gctttggtat tgtgggtta tgtactttgc   17640
agttttgata tttattagaa gaaaaattac tttaattctg gtaatactaa tgcttaccct   17700
gctcttctt gctagaatga tcagtcaact ggagatataa aagtcattgg tggggatgac   17760
cttcaacct tgactggaaa ggtatggcat gtcatatgtt taaagcaacc ccctcccccg   17820
cagaaaaaaa aatcctaaaa aatcctaaaa aaaacaaaa caaaaccaaa aaaaacaaaa   17880
caaaacaaaa ccaaaaaaaa aaaaaacacc aaagaaccaa ataattagag ttttagaaag   17940
gaaaaaaaaa aaaaagaaa gaaaactgta gtgtttcatt taaaatttag gttagaggtt   18000
ggacttgatg atcttgaggt ctcttccaac ctagaaattc tgtgattctg tgattctgta   18060
aaatattcac cattgtagag tggtggggtg cataagcccc accagagcca tcagtttagt   18120
ttgaacttca taacatatgt atgtatattc actgtcttca gtatcaggaa gtgttagagt   18180
tgttttctg cattgcctaa gaatagtctt gtcttggttg ttgttaacaa agtacccttta   18240
aaagagagta gcgttactta ttactgtgtt ggtgtttcat tgcaatagtg aacagagttg   18300
gtactgtcta gacatataac ttgcaggtta gggaataagg gtcctgttac aggcaatgaa   18360
gagacagaaa tgcagagaat gtaaattggg aatctgcttt tcttcagtgg ctgtgtagag   18420
atcattgagc tagatatctg tgggtaaaac atggatgcct cctgttctgt cagaacacat   18480
ggctttcccc ttctgattac acataaacag tctctgtccc atttcagtgt aagtgatgta   18540
ggtgtgacaa gacagtacat aactttatag tatgacattc tctgcattat aagaatttaa   18600
aggccacttt gtactcagca tgagatgttg aggcaagtct cattgtcaac taattgtcat   18660
tagagcatca gaaatgttaa ctaaatagaa ttcactgtta tgtgtcctaa catacataaa   18720
ccatggtaca aatatttaac tgcattgaaa aataaaattat taagttatag gagacaatat   18780
atgtaagaaa tgctgtattc tttaaatgct aatggattct tcttttttt tttttctttc   18840
```

```
caccagaatg ttttaattgt agaagtaagt attatgtttc actttgaagt tctaacgtgt   18900
gactggcaaa agaccttaaa cagaagttgg ttttaagtca gaaatcctac agtttctggt   18960
ttcaaggttt ttagtttctg actctaggcc tgaattatgc aagtggtctc tgaatttgaa   19020
attacctgtg ttttgaattc tcacatagca ttcaactata ccaaatttaa caaggaaaat   19080
atctgtgtaa aattgcttgc tgtttgcatt tgatttcagt tttctgtgat tctgtcaatt   19140
cttaaatgtc tttttttttt ttttaataat tcttattaag aagtagcctg agcaaagtgg   19200
tactaagtgt gttattgttc tgagtttata acagcaaact aggaaattaa actggagggg   19260
tagaaagaag ttcctagtag gaatatccta aaatacatgg gaaaacagag ctaaggccaa   19320
catctctgtg tacagtttct ttacaggcat ggagaatgtt gattcctaat ttgcattttg   19380
ataatgctta attcccattt ctctatcttg tcgtggttct ttgatactag gtacaataca   19440
cttcagtctg atttcctagt agctactgtt gcttaaatct tgcttccata cctctttgat   19500
gaacgatgtt gcttacattc agtaagtatg acttttacaa aggatgatct agaataagat   19560
cgctaacttg aggttggcaa agcagaagta ctaaacagga aaaatgaatg tatagaagta   19620
ataatgtctt cagactccaa atagtggaaa tggctttgtc cataagctat ggcaactgat   19680
tcagacacca aatgaaagga tgtttccttc tgtcattaaa tgtgtttttt ttatgtacgt   19740
ctttttttaa tttgagaagg ttatattatt ccataggaaa cacttttgac ctaaactgtt   19800
ttagttcagt tctaaaactc ctaccaaact agtatgtata cagcagtcat ctgtgtgacc   19860
ggtggcgtcc tttgaagtgt atttgcttca gataggcaga tgcatttaat tacgtatctg   19920
ctccatttca gatgaatgta tgtcttcaaa gtcccaggca gctaagtagg ttagtttctc   19980
atctgttcag tgaatcatct ctccagtgcc ttatatataa ttatacattg tcaaatatga   20040 acccttttgac cagtcaccgt tttaactgtc aaacaatggg ggaaaacaaa caaacaaaac   20100
caaaaaacat tattataggc accagagcac ttaggttttc catacagaat cccctttgatg   20160 tataaaaaca aacaaacgaa aaagaagaaa agaatcccat ccctttctgt gcagggggatg   20220 ggattaagat ggtgtgtcaa acatcattt agtgtatata aatagaaact ttagaactgc   20280
acccagatat tgccagtgca gcttctttgt ctttggattt ttttgggtct gtaatgtaag   20340
ttgcacttct ttttcctttta attgcattga tgggttgttc tgaatgtttt cccgtcttat   20400
tttctttctg ttgtatacat ctctctctga gttcaactgc aagactaatg ttccatttat   20460
aatactggaa ttaaacaatg tttgtcaaat agctacaagg aacacaagcc ataaactctt   20520
cagagggagc ctagaaggtc atagttcagt aactgctttc aaagtagtag ttatctacag   20580
ttttgactgt tgtgatcact ttactgagca taattgctta agcacaatat agcgttatgt   20640
atcacctgta tttgattatg aacattattt tgtcatattt ttgtgctatt acggatgagc   20700
aatttctgca gtaaaaactt gaaaatgcta ctctgaaaat tttaatattc tcacttacat   20760
gacactttta ttttcaggat ataattgata ctggtaaaac aatgaaaaca ttgctgtctc   20820
tactcaagca gtacaatcca aagatggtga aagtagccag gtaaacttct aaatgtgatt   20880
atttgtgctg tatttcaact tcagaatgac acacagtgga ataaaaatat aatatagaat   20940
atattcccat agaagagaaa caggaaggaa catttctgca ggaatcatac atgatggagt   21000
tagagttcag tatttgttta aactcaactt ctgcttgttg tgggagcata tgttcattaa   21060
ggctaacaga aatgctcttc tttccagtcc tattgcttga aaaatatcag tgccttatat   21120
tctagtaata tttgtggggt tttaccactg atctttaact taggtttaaa agcatatgga   21180
```

```
agaatttaaa tattttgggc ataaaaaaac acaacaacct ctcaaggtgg caggggtatt    21240
ttcaacacaa atttagttca taaatataaa ctttataaat ataaagttta actagagatt    21300
gggattaaaa aaaaaagtca gtggttgacg tctatggaca tacagtatct gaacatgttt    21360
cagtttgcaa cttcattttt tttcagtggt gtatctgcaa tggagacctt tggtctgcca    21420
gctttacttg tagaattaaa ttagtttgca ctaaacatta ccgtttatat agagtatata    21480
gtgtagctga gcctcagagg tcattctgtg agtcacccag ccatatgctc ttttaggctt    21540
ttctacttag ttgcatcttt aatcagttag ttatgaaacg ttttctaatt aaataactta    21600
cagttagtaa gaaatgttga gggtaatatt aaccaatatc aacattcctc ctacttcttt    21660
ttaaattgca tcttttatgc tcctatgctg tgattgtgta ttttacaata aaagcataat    21720
gattgctggg gattagagat aaaccagaac tgtgtgtaaa atctaatcag ttgtgttgcc    21780
ataacaatgt caaggcagtt gttagatgta ctagagcagc tcttcttgat gataatgtgg    21840
ggatgacctg ctgaaggtga ggttttgtt tttttttct ccgtggcctg cttaaatgta    21900
ccagatttta aatatttgtc actgaatagt accttaacgc tacagtgtac atcacaagta    21960
gaatgcagca tgaacaaagc ctagcttccg attgttaaaa cctgttgcag tttgggtctg    22020
ccgaagacct gagcaagtaa gcgtgatcgt gctggatagc tttaagtgtc atgctcttag    22080
ttcacttgcc tttcttttct taattttgtt ttctttctct ctgacaatta agcagttgta    22140
gcagggagat gtgaattaat gctaatgtga ttttgggttg gtttgatcaa gttttatgcc    22200
actactcaaa ttaagactct caactagaag tttcagaaac tgaatgtcta aagacagaca    22260
aatgtcagga tgatggggtc atcttctgaa agtgtgcaac tgaataatga gtgagtcaaa    22320
ttaaactaga aaggtatttc attctgctac agtaccccca actctgcatg tctatgcttt    22380
ttacacctct gactattaat tctgtgaaag tggagctggt ttatatcagc ttatgatcat    22440
caaaaccaat tacattttct gtatgggggt aattagtact accagtggaa aaacagctga    22500
ggacatgttg cacaagtgca attgaggtta catttaacca gctgaacttt tgcttcataa    22560
cactaacgct tttgaaaaga cctcagctgg tctggctaga tcccaagttg tcacctcttt    22620
acctgcgagc taaactgatt gcacctgagg tttctaaaaa cacataaaac ctaattaagt    22680
cacttctggc aatgaaaatc cttccagtaa agtatctcac agcctctttg ctgcaaacat    22740
tttgtttatc ccttaggctg taaaccattc atgattctag gaagttttga gtttgtctat    22800
atgatcagct gcacctgcaa atgaataata tgtttaaaat gtatatagtt atgctgtcaa    22860
ttatacacat gtagtctcac tgaagtggaa ttcagctaat cttcgtgttt catataagtg    22920
aacctggtgt ttttccacgt ttcagtttta cattgttttt atttgacagt tgttggtaa    22980 aaagaactcc tcgaagcgtg ggatatcggc cagactgtaa gtgactttt gacacccatt    23040 atcagttttt aaaaatatgt tgtatatatg ttgatgtatt gtgtactctt tggtcaaagt    23100
ccaagggtgt tccaagtaag ttttcatgaa tggttttga tttatttgc tcttatttgg    23160 gaagtttaaa tatttggaat gtattttgac agagttaata cagatttggt ctagtccttt    23220
ttttcttaac ttttgtggc atttattat acaaaaagga aactttgata ttttagtcca    23280
agttaatccc tcttcatatg gaaattctcc tagcttgcac gttaatcaaa tggtttggtc    23340
agcagaagtg tcatctttga cacttttggg agtgttccag gtgcctaaac atagccaccc    23400
agtgccactc ggatgtcccc agaaatgtaa tgggaccaca cagggtaaca gatctgatca    23460
aagtttacag tggtaagatg ttcaaagtag cacaaacccc atcttgttta agcatctgga    23520
ttactcctgt catgtcttct tgtctgtccc aagaccataa aggaaggaag agcatccaaa    23580
```

```
gcacacgggg gtgtcagtga tagcccctct tggcttggaa agggctacgt gtgctatccc    23640
tgtgccagag gttatttcct gttcatgtgg actgtgcgct ttcacaatgg aagtttaaca    23700
gaattgcatc ttcttcccc tccttcccaa gtttgcacag tattcttaaa ttgaaatttc      23760
tcagtgcctt gaaagcttaa ttcaggtgtt tccctcactc gaggatgcct ctcttcctg      23820 agatcttatt atgggtttag ctgggttaac agtctgcctt tctgagcatc ttgcagcaga    23880
tgacttgttt tgccatctgt ccagagacga cctgttcagt gcagaacccg tgagctctga    23940
aggcaagaga caacgcagca gcagagcttg ggcctgcctt ctgtccttgt atcatgaggc    24000
caagtagact ctaaacattg ccttattttt tccagaagcg tacacagtct ttcactggaa    24060
ttgtgtgatt tatctccgtt ttttcatta ctgagcctcg ctgtaaccag ggagagagaa      24120
acagcacagc tcgggagtct ttcatgttta gcataagggg agaaagcctt ctggaaacgt    24180
ccttaggttg tcttacagtg tgtgtggatg gcttggactg atacttcttg actatccaag    24240
gactgttctg ctagagccat gtccacttgg actatctgtg gaacagctga tgtgtttttt    24300
ttaggcagct tctatgggaa aaaaaaaaa cgaaacaaaa cacaacaaaa aacccgccgg      24360
tttctgaaaa gtgcaagtga caccgtaaat aagagagcgc ttttaccct gtggtcttca      24420 ctattctcta taccaagggc ttggcactta cagcgtgttg ctctgcagag ctgtcccgca    24480
gtcagagtat gtcctggtac accaggttgt tgtccacgag cagccagagg ggagtgaatt    24540
ttgtttggca ctgcctcaaa gacaaaggac tggttcccct gcggtaactc tggttcctcc    24600
tggtgttgac gtgttccatg cttactctcc cagctcttca caaagagccc agttgggctt    24660
gcacacctgt agttttgagg gagctgagag ctgaacctat ctgctcgtta tcccagaggt    24720
gaccttactt atagctgtgc ccaaggcgag ggcacactca cacaggtgcc acctttgaa      24780 taatactgtg agggtgacaa ctaaaacaaa ataaaatgct actgcttggg aaccagtaag    24840
taaatctatt tcatttgtt ttagttgaat taaatcaaca aatagagtta gaccattaac      24900
tagcttgaat attaatctcg ggatacttga atggaagaaa tgaaatgtta tgcttatatg    24960
tctataaaat tctagattct ctctgtaaaa aggtctagtg aactctagga agttcttttc    25020
taacatactg atgacttatg ttctttttca gttgttggat ttgaagtgcc agacaaattt    25080
gttgtgggat acgccctaga ttacaatgaa tacttcagag atttgaatgt aagtaacttt    25140
tcccgtatgt ttttgtccat ttaaaactag ggaggaggaa ggaagggaag tctcctcgca    25200
tcactctttc tcttctgtgt aaatcacagc tcatgtgcaa gcctgttcca ttagtgatgc    25260
aacgacgaga gcaaaggcta gaccagcaca acagtgtttt ggagctcata tgaaactaac    25320
ttttgttttg cttcatgcag aatggaggta ttctgcatga agctgtcagc tttgaaatac    25380
tgtggcagtc tgtatgaagt ttcttatctt accagacata tctgcaagaa acaagtgcat    25440
ttccttagtt acatcaaaat tagagaggag agaccttgga tgttgagatg tttgcatttt    25500
atgctaggtc attattaatt tttcatctgg gtctcactaa ccttataaca gacatagggt    25560
aggagagaga gagaaagtcc agtgttgaga tctgtagaca aaaaaaaaaa gaagctaaag    25620
tttttctgca taaacaatat cacaaggctc ttcggtactg aaatgtgtat agcatgcttt    25680
tatttttttc agaagtgcat tattgaatac atctgtaaac atcatcctac attactttct    25740
aacaggagct ttttattttg ttttgttaca gcatatctgt gtgatcagtg agacggggaa    25800
gcagaaatac aaagcatgaa agcatagttc aagtgctctg atagcagagc tttgaaatgt    25860
tttgtttact gagtcctatc tttcacaggc ttcaactctg gtacaccagc taaaattgta    25920
```

```
gaattatcca ccccccttgt catatgctta ctataactta ttgcatgtac aatatacaaa   25980
tcttgtcttg ttcatttata ttttagaaat gtaaacaatt agtgcaattc tgcactcctt   26040
attttgattt gcactatgac tctaccgact attgctgccc ctggttgggt tgtgctgttt   26100
gtgagctccg gagtctaact cttgcagtgg taaattgctt aaacctcatc aacccagaac   26160
tgaaatagtt caagtactgt aaatgtaaaa cactttatga tagggaagtc tattagtaat   26220 attttaaaa tctgtaattt aagttttata ttttcatgaa caagtgtgat tgtgattaat   26280
ggatagttgc acctttgggt gttataaaac atgaggagca gccagttaca gtatctgtaa   26340
tcaccaagga gctgattcaa gcctcctgga gttgccttat cgctgtaaaa gtccgggtaa   26400
aaaaaatctt ttttttttta atttttttta tttttgagc taaaaggaga tggaatgaca   26460
aagcagaatg tttaaaatct agtttaagtt gagctattca tttcttttgg atttttttctt   26520 taaaaatacc catcagacag tgaaattgcc ttttaaattt aaacaatttt aatatatttt   26580
tgaagaagta ttgtaatgtt tactttataa gatctaaaaa acaaaaagta ctttaaataa   26640
aggctgtctc tttaaaataa gccccataca tctatgccac tcattctgta tattaaagtg   26700
ctcttgaaat tttcttagta atattttca taagtgtttc tgacagtgaa ggcagactct   26760
acgtttgtta tctttgtaga gcctttagtc agtattgtgc catctacaag agatgataaa   26820
ggcctgaggg aaagctatcg aaatacttgc gtattctata accaaactgg atttcagaga   26880
aaatgcacta agtagtgtcc cgtattctgt tttggc                            26916

<210> SEQ ID NO 4
<211> LENGTH: 18700
<212> TYPE: DNA
<213> ORGANISM: Cairina moschata

<400> SEQUENCE: 4
agcaaaacga agaattgctt ggaagatgct tggttttgtc caaataaata gctgctgaga     60
gtgagagagt gagtgagtaa tattcagtat ttttaaagtg tcgagaaatg taatggggaa    120
aaatttaaaa taaatgttttt ttgtttgttt taaaaggagc tgtgtgcttt tatgttgaca    180
tgttgattta attactgcgg taggtattta ctgtgccctg ggaaacggta tccccagtca    240
acacagactt atttgtcagg aaaaaaattg tcatagatca tcttcaaata agagttgaca    300 ataatcaaa tcttgatgga gtataattat taatactgtg attacatatc catctttgca    360
agggtttcct gaaaaggtca gttttaagtc ttctattgtc aaatctgatg tttggagtag    420
ttcgctacat ggtgtttgat gccatgtaaa tagttaccag atagacgttt tatttttatgt    480 gctgtatgtt tttgtttttc attcagtcag ctggaatcat tgaaacagag aaggtttctc    540
aagaaatatc ctgaacctgt tttgtggatg tcttcattgc aatagctggt cactgaaatc    600
ttggaataac gacagaggaa tccataggca caggaccaaa caccttttcat tgtcctcata    660 tagcgtgatg ttagggcaga gtggtgagta cttcagtggc tcctgtgtcc atgctttaat    720
gaactctact taatctacca tatgtaagag acttgcagca caggcaaaac aagggaagtt    780
atctttgtgc ctagataatg taccacatat ggtaaacaat tttcaagcct cagagacaaa    840
agaaggatgc tgtaaagtct caagtctcag cttgtgtctc tgtttccacc tttctgttct    900
ttctgttcag acctctgggc cagtaattta aactggaaaa ttaatggaac agagaaactg    960
tttgtgagcc tatagaaaga tcaaattgtg tcagagtaat gttgctcctt ctacacccag   1020
ataaactttt tgagcagagg agaagcagtg aacagagctt tacttcatg actttgcata   1080 agaaaacatg ggaatgtggt ccgagaccaa tttaaaaata gaggttttga aaacttgttt   1140
```

```
ggaaaacaaa acttgcttgg aaaaccctat tcagagctgt gaatcattca cagacaacct   1200 cttaggggttg tagccactca tcagctgaat atgattcaac gatatgctga aaaaaaaaaa   1260
cacaaacatt gttgtggaat gtatgaacag gaatgtagtc tgtaagatgc gtgtcttggt   1320
ccttcttctt taggtaatag tagaacacct ttctgggaaa atggtatcca gctgttgtag   1380
gcactgcact ccatggaaaa tgtgaagaaa gtggaaataa tccagagaaa agcaatgaga   1440
gggatgacag gataaaaaat gagccttgct ttaaggtgat gagagaaaag tgttttcaa    1500 atctgtaaga gagccacaga gaagaaagaa agaaacagtt ctcatcattg caggtaggac   1560
aagaaaaata ggtttaagtt gctgcaggaa gcctttagct tagacatcag aatgggtaat   1620
tgtccttgac agtaggaaga attaagctgt agcatgcact tcctggagag gtcgtggaat   1680
ctcaggaatt aggttttaaa gggaatattt gtaggcatct tttggggctg gtgcaattgt   1740
aggttggagg tgctggggat aaggctaatg gaaatcccta ccagccactc taaggccttc   1800
tgcaaggagt cagaaccact tttcggaagt aaaactctgt actggcagag gtcctgtgct   1860
tgaccttaag gctcagagcc atgcatttcc gttttcatct tttcacttaa aatagcactt   1920
gtggtagtaa taacatgctc ttgcggagtg gcacaggtct gcatggttat gaactttctg   1980
tcaccaccca gcaaatggca ttttccactc ttctgtttca gattttcggg agtacttcct   2040
tactcccaaa ttcctgattg aatacgactg aaaacttcaa cacgttttta gtgcacgaag   2100
tgtactttat acaaatgtgt gggactattg cacacaactt actgattttc ttcactgtgt   2160
gcacatgtgc tctgtgatga tacagagttt ggggtgactg aactgttacc cagtctttac   2220
cgaattaggg cagcgatctt aaaccttcat ctgaactttt gctagagatg atcttctatt   2280
ttgtttagac agggttctct gcttgcttgc atttgttcta aaacgacagt ctggatgaga   2340
agaaaccaac cagggctggc actgccctac cttttattcc ctggatactt tacttggcac   2400
atcacttggc acacatgcaa taccttttt tcaccccggt acccaaagaa aagacgtgct   2460
cctgcacaga ctcagccaaa ttcctgcctg ccagtggagg gcgttacaga ggcttggggc   2520
agagggagga aactcactcc caaagcatat actaaaaata ggccaatgca ttgcaaacag   2580 cttttgctgtg agagcttcct tctggcatgt agccatgcag ctgccttata gttttgagcc   2640
tagatacctc caaaacaaaa caaaaagtcg ctaaagttaa atgcagccag cagtgcttat   2700
agtcttgata atccctacag tgtatcaatt ttagtttctt ccagagtgca ggtagtttac   2760
tcaatttaac ttcaaatgtc tgagttacac cattgacacc attgtcaaga ctagtgctgg   2820
caatccctga agtctgccaa gttcaaagca gggaggaggc ctttaaagtt gaaatactcg   2880
ggtgacgtgt ccaaaaagtt ttcctgtggc tttcctgtgg agtaggaact gcagtagcta   2940
ggttgcaaaa agttttttaaa ctctccaaat tgctgctaac taaacatcct taaatcctga   3000
catgagagta tgaaatgaga aagtcagttc cttgatttag actagcttga aaagaataaa   3060 cttttttgcac aggactccct ggacagttgg gctggataat agaagtgatt cattcaggtc   3120
ttgatgccta caagtttctt gggttttgcc atattttcca gtgatttgtg acatcatttt   3180
tgccctaaaa taaatcgcat catgtcctgc cgtatgtttt gactatgaaa atggaggttt   3240
cggtttgaat accaaacttc gttgttactt ctttcagagg ctgttgataa aggaaaacgt   3300
gaagctttta tgtaaatgat catgatttct catttgcatc aagaatattt tccaaaatag   3360
tagttaaatc cctccaatga ttttcagcta tgtcacataa atcaccgaaa acacggtaat   3420
tttgcacggg tgtttttttct ccctttttttt attgtctaat actcagctta tatttgagtc   3480
```

-continued

```
ttctgtatcc aattacctga tttgtgtggc aattaaacag aagatcagcg tcattgtact    3540
tcacattctt tttaaactca tcagtagtat gaccacacta gttggtcttg taagtttgta    3600
atttaagatg tgcctggaag gggttcaaag agacaggagc agtagtgtgt ctcacttccc    3660
tttggaaagc ctttctgata ctgtcaagca atatttacat caaaagggaa ctgaattctg    3720
gtaaactttt ccagactcca agtaaaccga acaacctgag atttagataa accttggtgg    3780
atttaaaaac ttgatggtat cactgtctaa gacttgtgtt agcccatcag atattgcaga    3840
cgtatatttt gaggaaaggc tttcagttaa ttgataaaat taagagcaga gttttggcaa    3900
aaaaaaccgc catctctgct cagtacttca tggcatcttg aatttctgca gttagaggta    3960
caggtgctct gttctgcaat taacccgtgc tgttaattaa aatgtactgt ttgctaaata    4020
tgattagtgt ctggagccag gtagcttgaa aaagcttcaa gattatttct ttttaccagg    4080
accatcaagt ttttagccct ccctttagag gaaggttcag aggaggtcct atttaatctg    4140
tcccagaaga aaggctattt ctcccccttag aatgggggctt ggcagtcctt ttcagagcac    4200
ttttcatcct tgtctcatag ggatttttaa ggacagattt ctgaaaggat tttccaccgg    4260
gtaaagcggg atcctgaatg ggtgacagat aatacgtagg aattctggct tcctactgcc    4320
aggttgttta tcttgagatc ttaaaaatgg acttatttcc ctttttaagt gtaaactgag    4380
ttcttgaggc accttttcca ctgaagtatc tgactttgcc cttactgccc atctcagtct    4440
tgcacattta acccaaattc agatccaggg tgtggtgtta ctcctagaac agctcttact    4500
gtttgaggat ctgaatgact attttgccag cttgtgccat acaactcgag aggacctgca    4560
aaggggaggg gagtcctgat gggcagttcc ctcccagcct ggcatgcgct tcgtgtctcc    4620
gcttccctta taatctgccc agaaaagatt tctgaaatac ttgagcagct gccacaatct    4680
gcatgggagg cagcagcctt ggcatgtgag ctctgccacc tgatgcccgg tctgtactga    4740
ggcagtgcca gctggatctg caagcctcag cgaatacagc cttcgtcagc gagttctctg    4800
atcagattgc tgccttggag ccttttgctg gtcttcctca gctcttctcc tgttactcag    4860
atagccttac cacctcctct catcatcttt tgagtttcta tcctcacgtt acagccaggt    4920
aagcccattt acccatgctg atatcaacag gttccagatt tttaaaaaa caatcctgtc    4980 tggctcacag ctagggagcc tctagtgaca cagctaagtc ccctgcagcc atttagaaat    5040
gtttctggag ggatgcaggt acgtcttgca ctcaggtgcc taatgaaagc agattgacct    5100
gttcattcct tcgaaagcaa ctaagcaaag tggggaatcc catgtctctg ccccacttct    5160
gtgttcctga cggcaagacc tcctgccagc accaaccgcc tgtgtttgga gtcagccagc    5220
cttccgttct gactgaagtt gaaggtacag tacaaactgc tggctaaaag aagctgcttg    5280
acttgctttt ttaggaggct tgtcttgtgg ggaaaaaaaa aaaagtaca gataaattct    5340 gctgattcct tctgagtcac ccagcagcga tggcaaagct aggagaaaaa atgggatcac    5400
agagggattg atgaatggac agtgagtgac ctgaagatct aactcaaagg acgttacttc    5460
aagtgcaagt gtcaacatat aaatgctgag ttgttgtctc caagtacccc actgttgggg    5520
tatcctggtt accaagcaag gttttagtaa gtctgttcga aaagttacat acagctgaca    5580
ttcatgcagg ccatgatttg ccaggcctga gctctgaggt attcctggac ggttagagag    5640
gataaaataa tttagaagtc aggaaaccac tcagagacaa accattattt ataaaattat    5700
tttgccttct aaaagatgtg cgttccagag aaatcacaac gttggctcca acctttttgc    5760
atcatctagc tagaaaatgt gcagcttcca gataccgcca gatcacctcc cttgaccctg    5820
ccctggaaac atcaatggct cccataccag taagaacaaa actggtcatc tactaaatcc    5880
```

```
gttgctgatc tcagctaacc aacttcctgt aatatcagca aatatttctg cttttgtaaa      5940
tctgttcttc cttccataat ggggtgccag caggaatgct tgggatccag aaatgcgctg      6000
gttggcagga agaacaaaga aattgttcac ccagaagggc aaaaaaggac taatgctttc      6060
gtccgcttgg gagaagttgc acagaactta tgccaacaac ttttgcacgc aatcagaaag      6120
atgccgctgg atgttacttt aatagcaga cgttaatatc agttattaat tagaaatgtc       6180
ttcagtaacc agactaaaag cagatcctga aacactcctg tggttgaaca gtctcttgac      6240
agacactgcc cactgtccag taatgtcagg cgctctctga acttgacagg gcagctgctg      6300 ttttcccag cctctggaa ataggccagc tctgacatgt ttctgatatt agctgggtgt        6360
atttcattct gctgccctag gcagtttgat aaaggctcct tcctcctgct ccagagctaa      6420
cccacccaaa ctgtagccga gcacctcgct gcaacaaaac tgcactcgct agggttctgc      6480
ctgtttgctt cattaagatc tgcttaaatt gtttcgtaca aaggaacact caaactgatt      6540
tctgagccca agtagcagt gctaggtgta catcaggagt tgtttggcat gaagaaacat      6600
tgccatggca ctgtatgaat aaagttattt ttaagaatca ttatcccttc cttgatacca      6660 agtcttatg cggcagaaaa tcaaacttgg tctccaccct tacagaaagc agaggaatgc      6720
tttcagctga tagttgctta agctagaata taagaaacca tgaatttctg tgtgcactgc      6780
ggcattgccc ttcattccag acctacgaaa aaaacgaca cttttgttac tattttttc       6840 cttcccatat gagaccaggg gagctaccca ggcatttcca ttcttataat tttacctcaa      6900
gatcaaattt tctccaggca gttaaaggca gctgcaccg gagacctcgc tcagcctccc      6960
cttgcatccc acggagctgc gtttagtgag aaacctcccc cgaggtgacg ggctgcaggg      7020
gaccccttcc cacacgcgtc cccgtcccct ttctcagtgc aaacgcagcc accgccccctt    7080 gaaccctcct ccgggctctc tcggttcggc ggaggcagga gggggccgtg cccgccgccc      7140
gggagctcct cacagggccc gggcccggg gcggagcggc cgcggccatg ttgagggcgg      7200
ggagcgcgga aggcggcgcc ggggccgctg cggggcgcgg cgcctccccg ctccccgccg      7260
ctcctcgccg cccgcagccg caacaccggc cccggcccg gcgggccgcg ccatggcggg      7320
cgcggagccc ttcggcgccg tgctgggcgc cctgcggac tgctacgcgc aggcggcccc       7380
gctggagacc ttcctccggg ggctggggga gcggcgcc gaggaagccg aggtggtgcg       7440
ggacgacgac gccgcctgct accgcacctt cgtgtcccag tgcgtggtgt gtgtccccca      7500
cggcgcccgc gacatccccc ggcccttcag cttggagcag ttatctagtc agagcgaagt      7560
catctcaaga gtcatgcaga ggctgtgtgg gaaaaagaag aagaacatcc tcacatatgg      7620
atactccttg ctggatgaaa acagttctca cttccaaatc atgccgctct caaacgtgta      7680
cagctacctg cccaacaccg caacagaaac catgcgtatc agtggcctct gggaaacgct      7740
gctgagcagg atagggatg acgtgatgat gtatttattg gagcactgtg caatctttat      7800
gctggttccc cctagtaact gttaccaagt ctgtgggcaa ccaattatg aacttatttc       7860 gcaaaatgta gaatcagccc cagcgtttgt taaacaacgg ctttcaaagc acaaacgtag      7920
tagcttgctt aagtatacgc agaaaaggct aacgtttcac agacagtatc tttcaaagtc      7980
acgtcagtcg aaacgcaggc aaagacttga agctaatgtc tccagcatga aaataaaac      8040 cagcaataat atacaaagcc tagggtccgc tgctctggaa aaacagagta gctccaatgc      8100 aggttttgtca gctacagcac catccttaaa aaggaagctt gctagggaac aactggaagt      8160
cacggctaag agagcaagat tagaagagaa agagagggag gaacaggctt gtaatactgc      8220
```

```
tcctaatgta aaccagagta ttcccaagag gtatggaacc agctgtgtag catcacgttc    8280
tgtaagtctt attaaagaaa aatacatttc tcaaagaagt aacagtgata tgtctcgtcc    8340
ttctttagtt cacaattctc atcatgggaa gaagtctgtg gcagacaaaa gctctttcct    8400
gcaaggagct gagagtaaca gacatttaaa gcccagcatt gaaatgcaag caggatccag    8460
caggaagaga gtagagatac acaggcctat acctcggttg gattggatac caatcgaacc    8520
ggcggaaagt agttcttcag gacacaaaaa gcaggaaagt cccctagctc atctggcaga    8580
ggagttacca aatagggttt tgccatctac aatatacatt gacaggaagt tcttctgta    8640 ttctcgcagg tactggggg aacgtttccc aaaatccttc ctattgaatc gcctgaaggg    8700
tagtgaggca ggtgtaaagc gactaataga aacgatattc ttaagccaaa atccgtttgg    8760
gcaaaagcgc aaccaaggtc tgccacagaa aaaatggaga aagaagaagc ttcccaaacg    8820
cttctggaga atgagaagta cgtttcaaaa actcttaaag aatcatggaa agttccctta    8880
cgtagctttc ttgagacaaa attgccctct tcggatatct gaaaccatttt tgggaaaagc    8940 caagctgctc agtcgggcac cttttgcctgg gcaagcagag gctcacaagc aagcagaaca    9000
gcttgggaag gagcctgcta agcgtgtggc aagcagcaga tgcgaatctg gtcacaccaa    9060
cgtgcccagc agcgtacgcg ctcctctcgc agcatctgcg tgcgtggagc caggggggga    9120
ggagcagatc cctgcagagg cgtctgattc agtcctcagg gagcttctca aggagcactg    9180
cagccacttc caggtgtacc tctttgtgag ggagtgcgtg gagcgggtga tccccgccga    9240
gctctggggt tcaaaccata acaagcgccg gttcttcaag aacgtgaaag cattcatttc    9300
catggggaag tacgctaagc tttccttgca ggtgttgatg tggaagatga gagtaaatga    9360
ctgcatgtgg cttcgtctgg ccaaaggtaa tcactttgtt cctgcctctg aacaccgtta    9420
ccgtgaagaa attttggcta aattcctata ctggctgatg gatacgtatg ttgttgagtt    9480
gctcagatca tttttctata tcaccgagac catgttccag aaaaatatgc ttttctacta    9540
ccgaaagtgt atttgggcca agttacagga cattggaatt agaaagcatt ttgccaaagt    9600
acagctacgt cctttaactg cagaggagat ggaagcgatc catcagaaaa aataccttcc    9660
tatggcatca aagctccgtt tcattcccaa agtcagtgga ctaagaccca tcgtcagaat    9720
gagcggtgtt gttgaagcac aaacgttgag caaggaaagc agagcaaaga agatgaatca    9780
ctacaacatg caactgaaaa atctatttag tgtgttaaat tatgaacgaa ctataaacac    9840
cagttacatc ggctcttcag tgtttgggag agatgatatc tacaagaagt ggaagacatt    9900
tgttaaaaag gttcttaaat cagatggtga aattcctcat ttctactatg taaaggccga    9960
tgtgtccagg gcttttgata gcattcctca cgataaactt gtggaagtga tttcacaggt   10020
cttaaaacct gagaaaaaaa ctgtctactg catacggcgc tatgcagtgg ttatgatcac   10080
tggaagtgga aaaaccagga gttatacag gagacatgtt tctactttca aggattttat   10140
gccagacatg aagcagtttg tgtcccggct tcatgagagt acctcattgc gagatgcaat   10200
aatagttgaa cagagcttaa ctttcaatga gacaagtgcc agtctatttta attttttct   10260 tcaaatgcta aataataaca tcctggaaat tgagcgcagc tactacttac agtgctctgg   10320
aattccacag ggctcccttt tgtcaacctt gctttgcagc ttgtgctatg gagacatgga   10380
aaacaaatta ttcagtgggg tacagaagga tggagtcctg atccgtctca ttgatgactt   10440
tttgcttgtt acaccacact taacgcatgc aagaacttc ctaaggactc tagcaatggg   10500
cattcctgag tatggctttt tgataaaccc caaaagacg gtgtgaatt tttctgttga   10560 cgatatccca gagtgttccg aatttaaaca gctgccaaac tgtcgtttga tcccatggtg   10620
```

```
tggcttatta ttggatacac agacacttga ggtttactgt gattactcca gctattcctg   10680
tacttctatc agatcaagtc tttccttcaa ttcaaacaga acagctggga aaaacatgaa   10740
acacaaattg gttgcagtcc ttaaactgaa atgccatggc ttgtttcttg atttacagat   10800
caatagcgtt aaaacagttt tcattaatgt ctacaagata tttttacttc aggcttacag   10860
gttccatgcc tgtgttattc aacttccatt caaccagaaa gttaggaaca atcctgattt   10920
cttcctcaga gtcatcgctg agaatgcatc gtgctgctat tctatgctga agctaaaaa   10980 tccagggttt actttaggta acagaggtgc atctggcatg ttcccttctg aggcagcaga   11040
gtggctctgc tatcatgcct tcactgtcaa actgtcaaac cacaaagttg tttacaaatg   11100
cttgcttaag cccctgaagt tctgtatgac acagctattc cggaagatcc caaggatac    11160 taaggcacta ctgaagacag tgacagaacc atctatttgt caagatttca aagctatcct   11220
ggactgatct agagttccta gtctagacta gagctcgctg atcagcctcg actgtgcctt   11280
ctagttgcca gccatctgtt gtttgcccct ccccgtgcc ttccttgacc ctggaaggtg    11340
ccactcccac tgtcctttcc taataaaatg aggaaattgc atcgcattgt ctgagtaggt   11400
gtcattctat tctgggggt ggggtggggc aggacagcaa gggggaggat tgggaagaca    11460
atagcaggca tgctggggag gtaatggatt tggtagttta ttgagtaaag caaaggattg   11520
gcagtttctc actacaggct ttctataaga ctttgtagaa atctcacctt atttccttt    11580 cagattgacg atgatgaaca aggttacgac ctggacttgt tctgcatacc taaacattat   11640
gcagatgatt tggaaaaagt ctatattcct catgggctca tcatggacag gtttgtttga   11700
cttcagacag tacactgctc cagctgattc catgacactg gaaaaaacaa tcttccagtg   11760
atagttttgc tgcctagtga ctgtctaaac agattacatt taattagaga ctaagaaata   11820
cacatgttaa ttaactctct cttgtttggc ttcaaagagt ttgtacattt gcagttacgc   11880
tattgtttgg aaatttgtca attctcaaag aaatttgtgg tacgtagcag tctgtgactt   11940
tctttacagt gtttctttga tgttttactt aaagtaatta gaacacatta cttgttgtgc   12000
tagttcaatc taaaaacagt tatagtctct caaacatctt taggatatta ataagagtag   12060
attattaatc acattatgat aagacttttt catgttcatg tggtagataa ctaacaccca   12120
attttcccct actgtctgcg aaagacatta gcctttgcaa ataccaatct gtcacttgtg   12180
gttgctgaaa tgtatgattt tctctggaag ttttatctcg tgatgagaaa tgggtacatg   12240
aacctataag gtgttttgt tttactttgt gtaagtaaag tggaggagtt gctggagaca    12300
cagaaccact gaagagcggt tctgagtaga tcttgtgaat aggaatgctt ctagattttg   12360
catggtgctg tttgatcaga ttattacagt atttataata aaatgttttt taactttaca   12420
ctgaaagacc ctatatagga aagcattgga caaagtacag gtcattaagt agctgatgta   12480
aagtttgtaa tggcaggcat tctctgagaa acctgctgtc agctgctata ctgtaaatac   12540
ataccatgct ttctgaatta aattgcaaga taaatttaga aacaatgatc actgaaaaac   12600
tgttcagtgt tctcttgctc tgctttattg gcattatatt ttgcagtcag acaaattta    12660 ttcagcaaaa cataacgcta tagttgataa tttgagagtt ttcttgctcc tcagttagtg   12720
agagctgttg tcttttggt tgtgctgatt tattttgctc tctgcatgga agctgaacct    12780
atctttggaa gaagaaaaca cccttatgtc tcttatctga cagtaaaaca attcagggtg   12840
ttcagatttg ctttggctga gtatgatgta tgaaaacaaa gaagtttggc agtgttactg   12900
ttagattaac cttggaacgc aaaactttgt tgaccaatag tgggttaaag tgactgaagc   12960
```

-continued

```
attaggcaaa tatttctgag caaaatatgc ttccgagttt gcatgtgttt gctgttgttg    13020
tttgcaatac aaaatactgc tgccatagta agcaaactaa atgtgttaca acagctaact    13080
ctcttttttt tttttttgta taggacagag agactggcac gagaaattat gaagggcatg    13140
ggaggacatc acattgtagc tctctgtgta ctcaagggtg gctataaatt ttttgctgat    13200
ttattagact acatcaaagc actgaacaga aacagtgaca aatcaatccc catgactgta    13260
gacttcatta ggttgaagag ttactgtgta agtatctctg caataccatg caattttcct    13320
gtaaatttga ctaacttcaa attaacaaca gggatgattg agaattgcca acaaatgttg    13380
caaaagcttt gcctaagtac tgcctaaatt gtgctaattt tatacaaata gttaagacaa    13440
ttaaggggaa aaaagcagtc acaagctaac ttgttctttg tctatcttat atgatctggt    13500
ttctttcaga ctttatctcc tcggcccagt aaaatccaga gcaaagagac cctttccatg    13560
tcctttactt cttaaacaat ttcctctctg ccccctgtcc cacctctaaa actgtggttc    13620
tagaataata cagaggatag tcctacaaat cttattacaa aaacttaact ctaggaattt    13680
tcatgtggct tagacatcac tcaccagata ggaaaacttg aaaactgtga gcatggttat    13740
atttgggttc cctacctcat cttttgtttg gctcaactga acaatgaatg gaatgaattg    13800
catttggcca tgaggaaata ctagattcat aaaaacagat ttatggttag cggccactga    13860
atatggtgct acctttaaa gcctaggtct aggttgcctt ggctttatgc ttttggaaaa    13920
gaatttattt tcatttttgca cacaagtatt taacttaca gggaaatgga gcatgaggta    13980
gtatgtaaga tttttataag ggaagcatta gattacattg tgcaggtcaa aggaggaagc    14040
agatgtatgt tagtactgta tgcttcctga ctcagcaaca gcctagtcta gtgttttcaa    14100
gacagtattt gtgggtaatt tagatttttt ccataagatc acctgtagtg tggaaataat    14160
taagtttttt gatttcaatt tacggtgtca aaataaattg cttcttaagg tcatgctgtt    14220
agttctgtgt ctcgatgact gtgttttcca gtcagtagta taagctactt gtcatggttg    14280
tggagtagtg cctgctgcag tagaaaaaaa tagattacta agttggaaac tcaactgcat    14340
tgttcattta attaaaccag atagggggt acttgcagat ttaggttgga ctgtagaaga    14400
gcttcaaaaa tgcgctgctg ctgttgagcg atctgtaaaa atttcacctc gttgagtggc    14460
aaagctcaga ccagtcagag tttggccagg cctgtttgca gaaaagctgt gccagctccc    14520
aaggtgtgtg tgcagtgatg tcctggggct acctggaaac caccgtcatg tctgcagagc    14580
gtgctgcagt gactcagctg cactcttttaa agagaaggca aggccaggca gaaagggaca    14640
tgccagcctt tcgttacatc ttgcaagggg agagctgctt gacacacttt gtttctgctc    14700
cccacaaaag attcaggctc cctctaccag tccattcaac cacaaagcca ctacgtgccc    14760
acatacgctg tctgtaaaag ccacaacaga aaggtgaatg tctctattag aggataaatat    14820
ttgaaagaat aggaaataac tcccacccttt tttggcgagg aaatttgtat ttctgctttt    14880
cttcaaggaa cacatccaat aactttggtt tatttaaaat ataaggacta cacccttctg    14940
ctctctccac cttccgagta acttggaaca agctatggga taagtgttgt gaaacacctg    15000
gaaaaaatac tacattgcaa agcaaggctt attgtacagc atgtttttat tgttcatctt    15060
tatgcattag gcatgtattg gttctgctgc ttttatttttt tacaccgccc ccccaaaacta    15120
tagtgctttt atattaatag gaaactgaac agcaaaataa ttacggaagt tttaattctc    15180
tttttgtagt aagaaggagt aaacaaagag aaaagcagag aaatttacac agaaaggagt    15240
gtaagcagaa tgttttccat gaggtgttgg cttcagggtt ttggttttgt cagccaattc    15300
tgtaaaggaa tgttttcttg ttctatatga ccgaggagct ccagttactt gatggcccca    15360
```

```
ctagcagatt attacgagca tttcatttct gtcaactctc taaggtagtt attaatatcc   15420
agacttacgt tctttagatt gcataacttg atagactggg taagactgtc ctaacacaaa   15480
catgcgtgta attgattcac ttagttttcc attattaatg gtgctggaat gttaaatctg   15540
ctctgtagtt ttcattcgtg ctttactaaa cggaggagtc agcattctta atgatgggaa   15600
aaccatcaca aaccgtaatg gacagttgaa agtagagcta gctctcttgt gattgttgtt   15660
ggatgcaatt actagatcac gctgcctgcc tttacagact gggtgaaaga tgttaaaaat   15720
accgtcgttg cataaacaaa gcagctgaac tcgtataatg gttctaaaat tgatgcgatt   15780
gatgttctat tcctatttga aattgatcat ttaatatttt caagcttatg ggttatttgt   15840
ttcataatgc aaagttcata ctatgattgc acccaaaaat aattctctaa gaatactgag   15900
atgatgaagc tgtgattaaa tgttgcttat aattcctgct ttcggagtcc ttacaaatga   15960 gtttttaatga tctggcaagc tgttaagaaa ttgaaagata gtgtttgtga acagaaccag   16020
atctctgtat tcttgacaaa tagtttattt ttcttgtgct agaagaatgg cttttcacca   16080
gtttcctgca tgtaaagtta gagttaagca aaagttgctt atgtagtcac aaagggcagc   16140
caaaacacaa tggacgtgtt gcattgtcac tcagggaaat agggcttttc ggaggagtac   16200
tgcagcttta aggcaaaatc tagttaggct ggttgagaca gtattctgaa agatctcatg   16260
ttaactgagc cttatagcaa ataccatgag gaacttaaaa tgccttgtca ggggttacga   16320
tcttgcagca tgttattatt ttccagcaat gacaatgagg cagtgaaaac agatctaaac   16380
agtaaatctc taatgtgtta aatcacaaag cattaaagtc ttaccagtac tgaaatcaga   16440
aataatgctc ctgaagataa ttaaagtgtt gcttaattat taaacaaagt tctttccaat   16500
ggaaatctgg ttaaaaccag tgttggaaat ttgttaacca ttttttgatcc tttaattgct   16560 cagaaactca gtacctgcat aggcgtgtag gtttatatgc cagcgaaggt ttatgttttg   16620
tgttaaaaaa tgtagcaatt tgcagggtgc ttggtgggaa gaagaagggc agattttgtt   16680
ggttagattg tttttctctg ctgatcagtg tacttgagta tgcataaccc acagggttct   16740
gtagtgatct gtagttctgt gttgttattg tttgattata gtgtgttgct ttgtagccag   16800
agagatcacc aggaaactga tctgcatgca tgtactgaga ggactggtct atcatctgtg   16860
catggtgttt taatggaaca aatatctgta acatctttct ccatcttcct tctgtaagaa   16920
atggtgcttt ttcatccttt ccatggaaaa aggacgaaat tcttattagt gtaggaatag   16980
ataagagaga atcctgcaac ataaacaggg aaaagcttaa agctgtcatt taagataatt   17040
ttaagatatg atgaacgcag gaaatgcccc tcagcattac aaacacggtg cttaactgaa   17100
tcccattttc gtgattaatc taaccagtat ctctggcatt cagtagcagt ctgctgttta   17160
ctgggtcaag cagcagacat tttggacatc ctattttggg acttttttcaa cacagtggta   17220 ttggttctgt tcactatagt tttctttaaa acatgggtta aaactgtaaa ggcgcttttt   17280
ctaatgtgtt gtgcttgcct ttttttttaat gttttgtcat gggaatctaa aatagaaagt   17340
atctgttagt ctcgttatct gctttttacat acctagagct gtcagcactt ctttatccta   17400
gagcattgac gtcactgtcc aagggatttt aatacatttt ctctttactg taatcccagt   17460
gtcacttatg gtgtgctcag tgtgtgtttc tctctaaacc atttacccct tttttgcatg   17520
tgataacact tctactttt gtctgcaact ggtacagtat gaatatgtgt gtcagtgaaa   17580
acaggaagct gtatgtggcc gtctgttccc ctgtggtctc ctctctattg tatctgccat   17640
tttggggcgt ggggaaggaa ctgctctttt gctgcttgtc tgcatggtca tgcagtaagg   17700
```

-continued

```
ttgggcttca gactgaagcg gcaaaataat aaaggttttc taaagggaag atatgaagtg    17760
aagagctgtg agaatgaagt ttgaaaagtg gtatgaccct tcaaataaat gattaaattg    17820
taggataatg acatcatctg taagtagcac agtaatgagt atagcacaat taataagaac    17880
taggagacaa tgtcaaggtt taaagtcagc tgaatgactt taaataaact gcagagatct    17940
ggaggtaccc caggagttgt ttttaacttt cttatataac aaacagttca ctgatgctta    18000
catcaaagcc tagttttact aaagcaaaat gctgtacttc agtgatagga ttgtgtagct    18060
gtgtcgctgt ttaattacca caatgagtaa tttatcacta tttgtaaaat aggcaaaccc    18120
aagcttttct ggctattctt gtagcttata tttcttgttc ttaatctgtg ccttgtttgc    18180
tggctatttc attgttgtta tgattgctta tttttattca gagtaaggct ttctaaggca    18240
tcaaagttta aaatgtaaat taccagctat atagcagcgt acagcttgga aactttttt     18300 ttttcctgtt ttccatacct ttaatgaata tgtaggaaat aatatttttt taatatacat    18360
gtgtgtatat ataatggtga cagatgagaa gtggtgcctg tatttatgta aatatttttt    18420
caaacaatct tttatctgaa ataccatctt tcagtttgat tacttgtaat ttcttagtta    18480
atagatgttg ctggtgcaat gcttctgaaa gctttggtat ttgtgggtta tgtactttgc    18540
agttttgata tttattagaa gaaaaattac tttaattctg gtaatactaa tgcttaccct    18600
gctctttctt gctagaatga tcagtcaact ggagatataa aagtcattgg tggggatgac    18660 ctttcaaccct tgactggaaa ggtatggcat gtcatatgtt                          18700

<210> SEQ ID NO 5
<211> LENGTH: 18
<212> TYPE: DNA
<213> ORGANISM: Cairina moschata

<400> SEQUENCE: 5
tagggataac agggtaat                                                      18

<210> SEQ ID NO 6
<211> LENGTH: 18
<212> TYPE: DNA
<213> ORGANISM: Cairina moschata

<400> SEQUENCE: 6
atccctattg tcccatta                                                      18
```

AVIAN TELOMERASE REVERSE TRANSCRIPTASE

CROSS-REFERENCE TO PRIORITY/PCT APPLICATIONS

Figure 1:
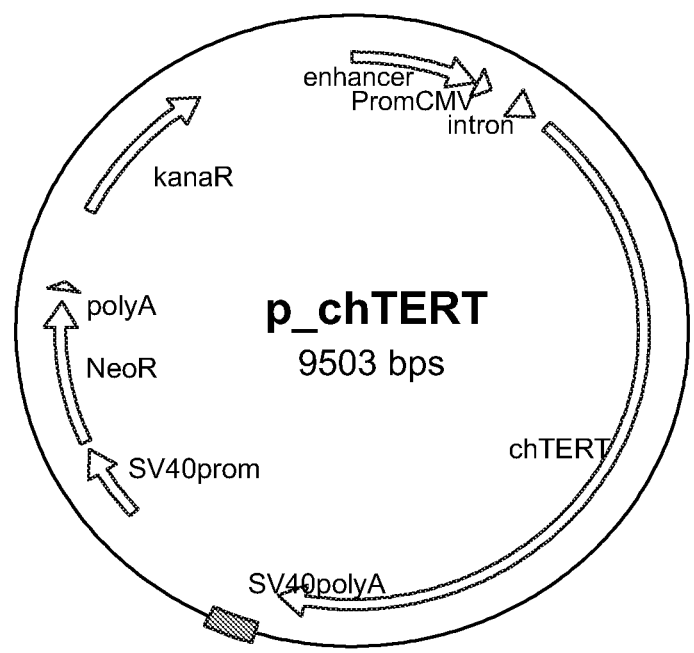

This application claims priority under 35 U.S.C. §119 of EP 06360047.2, filed Oct. 13, 2006, EP 06360001.9, filed Jan. 5, 2006, and is a continuation of PCT/EP 2007/050120, filed Jan. 5, 2007 and designating the United States as WO 2007/077256 A1, each hereby expressly incorporated by reference in its entirety and each assigned to the assignee hereof.

The present invention notably relates to novel recombinant telomerase reverse transcriptases, nucleic acid molecules coding them, cells comprising said nucleic acid molecule and use of these cells for the production of substance of interest.

In 1965 L. Hayflick discovered that cells have a programmed moment of death. As one explanation for aging, he suggested that the number of times a human cell can divide is limited (Exp Cell Res. 1965 March; 37: 614-36). This is now known to be caused by the shortening of telomeres as cells divide. Chromosomes are capped by telomeres consisting of a conserved, tandemly repeated, non-coding, hexameric DNA sequence associated to single- and double-stranded binding proteins. Telomeres are responsible for genome-stability functions and in particular replication of the chromosome termini. Successful chromosome end replication requires both the unique telomere structure and the specialized enzyme telomerase reverse transcriptase, which is a nucleoprotein having a reverse transcriptase enzymatic activity. Telomerase reverse transcriptase is capable to lengthen the telomere repeat array, allowing for extended replication of the complimentary daughter strand. In cells lacking telomerase reverse transcriptase, telomeric DNA shortens on successive divisions as the DNA-synthesis enzymes are incapable of completely replicating the termini of chromosomes once the initiating RNA primer is removed. Numerous works have reported the evidence that the so called "telomere clock" is an important feature of human cell lifespan. The telomere hypothesis of cellular aging proposes that shortening of telomere is related to a lack of telomerase reverse transcriptase activity over and triggers chromosomal instability, leading to senescence, apoptosis. Telomerase reverse transcriptase activity is down-regulated in somatic cell lineages during development in vivo and in primary cells in vitro correlating with telomere shortening. Conversely, upregulation or dysregulation of telomerase reverse transcriptase activity occurs in transformed cells and tumors. The telomerase reverse transcriptase (TERT) cDNAs from several mammals and one amphibian were cloned and studied (Nakamura et al. 1997. Science 277, 955-959; Greenberg et al. 1998. Oncogene 16, 1723-1730).

As TERT over-expression in a cell leads to the immortalization of said cell, the use of TERT for the production of cell lines has been proposed (McSharry et al., 2001 J Gen Virol. 82, 855-63). However, the TERT activity is specie restricted. For example, human TERT is incompatible with the avian telomere maintenance apparatus (Michailidis et al. 2005. Biochem Biophys Res Commun. 335 (1), 240-6). Therefore, to develop avian and more particularly anatidae cell lines, there is a need of TERT which perform in these particular cells.

Eukaryotic cell lines are fundamental for the manufacture of viral vaccines and many products of biotechnology. Biologicals produced in cell cultures include enzymes, hormones, immunobiologicals (monoclonal antibodies, interleukins, lymphokines), and anticancer agents. Although many simpler proteins can be produced using bacterial cells, more complex proteins that are glycosylated, currently must be made in eukaryotic cells.

Avian cell lines are particularly useful since many virus used in pharmaceutical composition are able to replicate on them. More noticeably, various viruses are only able to grow on avian cells. This is for example the case of Modified Virus Ankara (MVA) which is unable to grow on most of the mammalian cells. This poxvirus, which derived from a Vaccinia Virus by more than 500 passages on CEF was used in the early seventies for vaccinating immunodeficient peoples against Variola. Now, MVA is mainly used as a vector for gene therapy and immunotherapy purposes. For example, MVA is used as a vector for the MUC1 gene for vaccinating patients against tumor expressing this antigen (Scholl et al., 2003, J Biomed Biotechnol., 2003, 3, 194-201). MVA carrying the gene coding HPV antigens are also used as a vector for the therapeutic treatment of high grade cervical lesions. More recently, MVA has been the vector of choice for preparing prophylactic treatment against newly emerging diseases or probable biological weapons such as west nile virus and anthrax.

Therefore, there is a need for new Telomerase Reverse Transcriptase able to immortalize avian cells and more particularly Anatidae cells.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

As used herein, the terms "comprising" and "comprise" are intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The present invention relates to an isolated, and/or recombinant polypeptide comprising an amino acid sequence which has at least 60% amino acid sequence identity to SEQ ID NO:1. In a more preferred embodiment of the invention, the polypeptide of the invention comprises an amino acid sequence which has at least 70%, preferably at least 80% and even more preferably at least 90% amino acid sequence identity to SEQ ID NO:1. In a more preferred embodiment, the polypeptide of the invention comprises the amino acid sequence set forth in SEQ ID NO:1.

In a preferred embodiment the polypeptide of the invention has a TERT activity and in a more preferred embodiment of the invention the expression of the polypeptide of the invention allows the immortalization of a cell belonging to the Anatidae family.

As used herein, the term "isolated" and/or "recombinant" means that the nucleic acid molecule, DNA, RNA, polypeptides or proteins so designated have been produced in such form by the hand of man, and thus are separated from their native in vivo cellular environment. As a result of this human intervention, the recombinant DNAs, RNAS, polypeptides and proteins of the invention are useful in ways described herein that the DNAs, RNAs, polypeptides or proteins as they naturally occur are not.

In another embodiment, the present invention refers to an isolated nucleic acid molecule which encodes the polypeptide of the invention.

In a preferred embodiment of the present invention, the nucleic acid molecule encoding the polypeptide of the invention comprises substantially the same nucleotide sequence as the one set forth in SEQ ID NO:2. Preferred nucleic acid molecules encoding the polypeptide of the invention comprise the same nucleotide sequence as the one set forth in SEQ ID NO:2.

As employed herein, the term "substantially the same nucleotide sequence" refers to nucleic acid molecule having sufficient identity to the reference polynucleotide, such that it will hybridize to the reference nucleotide under moderately stringent hybridization conditions. In one embodiment, nucleic acid molecule having substantially the same nucleotide sequence as the reference nucleotide sequence encodes substantially the amino acid sequence set forth in SEQ ID NO:1. In another embodiment, nucleic acid molecule having substantially the same nucleotide sequence as the reference nucleotide sequence has at least 70%, more preferably at least 90%, yet more preferably at least 95%, identity to the nucleotide acid sequence set forth in SEQ ID NO:2.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature (Tm) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5*Denhart's solution, 5*SSPE, 0.2% SDS at 42° C., followed by washing in 0.2*SSPE, 0.2% SDS, at 65.degree. C.

The nucleic acid molecule of the invention can be a RNA, a cDNA or genomic sequence or be of a mixed type. It can, where appropriate, contain one or more introns, with these being of native, heterologous (for example the intron of the rabbit-globin genes etc.) or synthetic origin, in order to increase expression in the host cells.

The present invention also relates to a vector which carries a nucleic acid molecule according to the invention.

As used herein, the term "vector" is understood to mean a vector of plasmid or viral origin, and optionally such a vector combined with one or more substances improving the transfectional efficiency and/or the stability of said vector and/or the protection of said vector in vivo toward the immune system of the host organism. These substances are widely documented in the literature which is accessible to persons skilled in the art (see for example Felgner et al., 1987, Proc. West. Pharmacol. Soc. 32, 115-121; Hodgson and Solaiman, 1996, Nature Biotechnology 14, 339-342; Remy et al., 1994, Bioconjugate Chemistry 5, 647-654). By way of illustration but without limitation, they may be polymers, lipids, in particular cationic lipids, liposomes, nuclear or viral proteins or neutral lipids. These substances may be used alone or in combination. Examples of such compounds are in particular available in patent applications WO 98/08489, WO 98/17693, WO 98/34910, WO 98/37916, WO 98/53853, EP 890362 or WO 99/05183. A combination which may be envisaged is a plasmid recombinant vector combined with cationic lipids (DOGS, DC-CHOL, spermine-chol, spermidine-chol and the like) and neutral lipids (DOPE).

The choice of the plasmids which can be used in the context of the present invention is vast. They may be cloning and/or expression vectors. In general, they are known to a person skilled in the art and a number of them are commercially available, but it is also possible to construct them or to modify them by genetic engineering techniques. There may be mentioned, by way of examples, the plasmids derived from pBR322 (Gibco BRL), pUC (Gibco BRL), pBluescript (Stratagene), pREP4, pCEP4 (Invitrogene) or p Poly (Lathe et al., 1987, Gene 57, 193-201). Preferably, a plasmid used in the context of the present invention contains a replication origin ensuring the initiation of replication in a producing cell and/or a host cell (for example, the ColE1 origin may be selected for a plasmid intended to be produced in E. coli and the oriP/EBNA1 system may be selected if it is desired for it to be self-replicating in a mammalian host cell, Lupton and Levine, 1985, Mol. Cell. Biol. 5, 2533-2542; Yates et al., Nature 313, 812-815). it may comprise additional elements improving its maintenance and/or its stability in a given cell (cer sequence which promotes the monomeric maintenance of a plasmid (Summers and Sherrat, 1984, Cell 36, 1097-1103, sequences for integration into the cell genome).

As regards a viral vector, it is possible to envisage a vector derived from a poxvirus (vaccinia virus, in particular MVA, canarypox and the like), from an adenovirus, from a retrovirus, from a herpesvirus, from an alphavirus, from a foamy virus or from an adeno-associated virus. A nonreplicative vector will preferably be used. In this regard, the adenoviral vectors are most particularly suitable for carrying out the present invention.

According to a preferred embodiment of the invention, the vector according to the invention further comprises the elements necessary for the expression of the nucleic acid molecule of the invention in an host cell.

The elements necessary for the expression consist of the set of elements allowing the transcription of the nucleotide sequence to RNA and the translation of the mRNA to a polypeptide, in particular the promoter sequences and/or regulatory sequences which are effective in said cell, and optionally the sequences required to allow the excretion or the expression at the surface of the target cells for said polypeptide. These elements may be regulatable or constitutive. Of course, the promoter is adapted to the vector selected and to the host cell. There may be mentioned, by way of example, the eukaryotic promoters of the genes PGK (Phospho Glycerate Kinase), MT (metallothionein; McIvor et al., 1987, Mol. Cell. Biol. 7, 838-848), α-1 antitrypsin, CFTR, the promoters of the gene encoding muscle creatine kinase, actin pulmonary surfactant, immunoglobulin or β-actin (Tabin et al., 1982, Mol. Cell. Biol. 2, 416-436), SRα (Takebe et al., 1988, Mol. Cell. 8, 466-472), the SV40 virus (Simian Virus) early promoter, the RSV (Rous Sarcoma Virus) LTR, the MPSV promoter, the TK-HSV-1 promoter, the CMV virus (Cytomegalovirus) early promoter, the vaccinia virus promoters p7.5K pH5R, pK1L, p28, p11 and the adenoviral promoters E1A and MLP or a combination of said promoters. The Cytomegalovirus (CMV) early promoter is most particularly preferred.

According to a preferred embodiment, the vector of the invention further comprises two sequences which are homologous with sequence portions contained within a region of a target DNA sequence native to the genome of a cell genome. The presence of said homologous sequences allows the site specific insertion of the nucleic acid molecule of the invention into the target DNA sequence by homologous recombination.

The term "homologous recombination" refers to the exchange of DNA fragments between two DNA molecules at the site of essentially identical nucleotide sequences. Preferably, the homologous sequences in the vector are hundred percent homologous to the region of the target sequence. However, lower sequence homology can be used. Thus, sequence homology as low as about 80% can be used.

The homologous sequences in the vector comprise at least 25 bp, longer regions are preferred, at least 500 bp and more preferably at least 5000 bp.

According to a more preferred embodiment of the invention, the nucleic acid molecule is surrounded by the homologous sequences in the vector.

As used herein "surrounded" means that one of the homologous sequences is located upstream of the nucleic acid molecule of the invention and that one of the homologous sequences is located downstream of the nucleic acid molecule of the invention. As used herein, "surrounded" does not necessarily mean that the two homologous sequences are directly linked to the 3' or to the 5' end of the nucleic acid molecule of the invention, the nucleic acid molecule of the invention and the homologous sequences can be separated by an unlimited number of nucleotides.

As used herein, a "target DNA sequence" is a region within the genome of a cell which is targeted for modification by homologous recombination with the vector. Target DNA sequences include structural genes (i.e., DNA sequences encoding polypeptides including in the case of eucaryotes, introns and exons), regulatory sequences such as enhancers sequences, promoters and the like and other regions within the genome of interest. A target DNA sequence may also be a sequence which, when targeted by a vector has no effect on the function of the host genome.

As used herein, "inserted into a target DNA sequence" widely means that the homologous recombination process which leads to the insertion of the nucleic acid molecule of the invention introduces a deletion or a disruption into the targeted DNA sequence.

The one skilled in the art is able to choose the appropriate homologous sequences in order to target a specific DNA sequence into the genome of a cell. For example, one homologous sequence can be homologous to a part of the targeted DNA sequence, wherein the other homologous sequence is homologous to a DNA sequence located upstream or downstream the targeted sequence. According to another example, one of the homologous sequences can be homologous to a DNA sequence located upstream the targeted DNA sequence, wherein the other homologous sequence is homologous to a DNA sequence located downstream the target DNA sequence. In another example, both the homologous sequences are homologous to sequences located into the target DNA sequence.

According to a preferred embodiment of the invention, the target DNA sequence is the HPRT (Hypoxanthine phosphoribosyl transferase) gene.

The genomic sequence comprising the HPRT promoter and the HPRT gene of *cairina moschata* is set forth in SEQ ID NO:3. The sequence coding the HPRT start at the ATG codon in position 8695 of the nucleic acid sequence set forth in SEQ ID NO:3, the sequence upstream this ATG codon is the HPRT promoter sequence.

The one skilled in the art is able to choose the homologous sequences necessary for the integration of the nucleic acid molecule of the invention into the HPRT gene. As between the various members of a family, the genomic sequences coding HPRT are highly homologous among avians, the one skilled in the art is thus able to design the homologous sequences necessary to target the HPRT gene of other avian cells.

According to a more preferred embodiment of the invention, the homologous sequences are customized in order to insert the nucleic acid molecule of the invention downstream the HPRT promoter. In this particular embodiment, the nucleic acid molecule of the invention is operably linked to the cell's endogenous HPRT promoter. In the context of the present invention, "Operably linked" is intended to mean that the nucleic acid molecule is linked to the promoter in a manner which allows for its expression in the cell.

According to this particular embodiment, the homologous sequence, upstream the nucleic acid molecule of the invention, has preferably a nucleic acid sequence which is homologous with at least 500 contiguous by and more preferably at least 5000 contiguous by of the nucleic acid sequence starting from the nucleotide at position 1 and ending with the nucleotide at position 8694 of the nucleic acid sequence set forth in SEQ ID NO:3, with the proviso that said homologous sequence is not homologous with the nucleic acid sequence starting with the nucleotide at position 8695 and ending with the nucleotide at position 26916 of the nucleic acid sequence set forth in SEQ ID NO:3. Moreover, this upstream homologous sequence is preferably directly linked to the start codon of the nucleic acid molecule according to this invention. According to an even more preferred embodiment of the invention, the homologous sequence upstream the nucleic acid molecule of the invention consists in the nucleic acid sequence starting from the nucleotide at position 1383 and ending with the nucleotide at position 8694 of the nucleic acid sequence set forth in SEQ ID NO:3. For example, the vector according to the invention comprises the nucleic acid sequence starting from the nucleotide at position 1 and ending with the nucleotide at position 11227 of the nucleic acid sequence set forth in SEQ ID NO:4. The homologous sequence, downstream the nucleic acid molecule of the invention, preferably has a nucleic acid sequence which is homologous with at least 500 contiguous by and more preferably at least 5000 contiguous by of the nucleic acid sequence starting from the nucleotide at position 10581 and ending with the nucleotide at position 17800 of the nucleic acid sequence set forth in SEQ ID NO:3. And more preferably, said homologous sequence, downstream the nucleic acid molecule of the invention, consists in the nucleic acid sequence starting from the nucleotide at position 10581 and ending with the nucleotide at position 17800 of the nucleic acid sequence set forth in SEQ ID NO:3.

According to a preferred embodiment, the vector of the invention comprises a first selection marker, wherein this first selection marker is a positive selection marker and wherein said first selection marker and the nucleic acid molecule of the invention are positioned in the same section of the vector, said section being delimited by the homologous sequences.

As used herein, the term "positive selection marker" notably refers to a gene encoding a product that enables only the cells that carry the gene to survive and/or grow under certain conditions. Typical selection markers encode proteins that confer resistance to antibiotics or other toxins, e.g., ampicillin, neomycin, methotrexate, or tetracycline, complement auxotrophic deficiencies, or supply critical nutrients not available from complex media. In a preferred embodiment according to the invention, the first selection marker encodes a protein that confers resistance to antibiotics.

According to a more preferred embodiment of the invention, the first selection marker, in the vector, is surrounded by sequences allowing its suppression. Said sequences allowing the suppression of the first selection marker do not surround the nucleic acid molecule of the invention. When the vector is circular, the sequences allowing the suppression of the first selection marker, the first selection marker and the nucleic acid molecule of the invention are positioned in the same section of the transfer vector, said section being delimited by the homologous sequences.

Sequences allowing the suppression of a nucleic acid fragment are well known to the one skilled in the art (Nunes-Duby, S. et al (1998) Nucleic Acids Res. 26:391-406). These sequences can be recognized by one or more specific enzymes which induce the suppression of the nucleic acid comprised between said sequences, these enzymes are called "recombinase". For example, three well-known recombinases allowing the suppression of a nucleic acid fragment are the FLP, ISCEI and Cre recombinases.

A typical site-specific recombinase is Cre recombinase. Cre is a 38-kDa product of the cre (cyclization recombination) gene of bacteriophage P1 and is a site-specific DNA recombinase of the Int family. Sternberg, N. et al. (1986) J. Mol. Biol. 187: 197-212. Cre recognizes a 34-bp site on the P1 genome called loxP (locus of X-over of P1) and efficiently catalyzes reciprocal conservative DNA recombination between pairs of loxP sites. The loxP site consists of two 13-bp inverted repeats flanking an 8-bp nonpalindromic core region. Cre-mediated recombination between two directly repeated loxP sites results in excision of DNA between them as a covalently closed circle. Cre-mediated recombination between pairs of loxP sites in inverted orientation will result in inversion of the intervening DNA rather than excision. Breaking and joining of DNA is confined to discrete positions within the core region and proceeds on strand at a time by way of transient phosphotyrosine DNA-protein linkage with the enzyme.

Another site-specific recombinase is the I-SceI. Other intron-homing endonuclease, for instance I-TliI, I-CeuI, I-CreI, I-PpoI and PI-PspI, can also be substituted for I-SceI. Many are listed by Belfort and Roberts ((1997) Nucleic Acids Research 25:3379-3388). Many of these endonucleases derive from organelle genomes in which the codon usage differs from the standard nuclear codon usage. To use such genes for nuclear expression of their endonucleases it may be necessary to alter the coding sequence to match that of nuclear genes. I-SceI is a double-stranded endonuclease that cleaves DNA within its recognition site. I-SceI generates a 4 bp staggered cut with 3'OH overhangs.

The enzyme I-SceI has a known recognition site. The recognition site of I-SceI is a non-symmetrical sequence that extends over 18 bp.

```
5' TAGGGATAACAGGGTAAT 3'      (SEQ ID NO: 5)

3' ATCCCTATTGTCCCATTA 5'      (SEQ ID NO: 6)
```

Therefore, in a preferred embodiment of the invention, the sequences allowing the suppression of the first selection marker comprises the recognition site of I-SceI.

Another site-specific recombinase is the FLP recombinase. Flp recombinase recognizes a distinct 34-bp minimal site which tolerates only limited degeneracy of its recognition sequence (Jayaram, 1985; Senecoff et al., 1988). The interaction between Flp recombinase and a FRT sequence have been examined (Panigrahi et al., 1992). Examples of variant FRT sequences are given by Jayaram (1985) and Senecoff et al. (1988), and an assay for Flp-mediated recombination on different substrates is described by Snaith et al. (1996).

In the particular embodiment, where the vector of the invention comprises sequences allowing the suppression of the first selection marker, said vector can advantageously comprises a first homology sequence A and a second homology sequence B, wherein the homology sequences A and B have a sufficient length and a sufficient homology that allows for homologous recombination between them. Referring to the homology sequences A and B, "sufficient homology" preferably refers to sequences with at least 70%, preferably 80%, by preference at least 90%, especially preferably at least 95%, very especially preferably at least 99%, most preferably 100%, homology within these homology sequences over a length of at least 20 base pairs, preferably at least 50 base pairs, especially preferably at least 100 base pairs, very especially preferably at least 250 base pairs, most preferably at least 500 base pairs. In this embodiment, the vector of the invention comprises in the 5'- to 3'-orientation as follows the nucleic acid molecule of the invention, the first homology sequence A, a sequence allowing the suppression of the first selection marker, the first selection marker, a sequence allowing the suppression of the first selection marker and the homology sequence B.

According to a preferred embodiment, the vector of the invention comprises a second selection marker which is not surrounded by said homologous sequences, wherein said second selection marker is a negative selection marker. Said second selection marker is particularly useful when the vector of the invention is circular. When the vector is circular, the fact that the second selection marker is not surrounded by said homologous sequences means that the second selection marker and the nucleic acid molecule of the invention are not positioned in the same section of the transfer vector, said section being delimited by the homologous sequences.

According to a preferred embodiment of the invention, the vector of the invention comprises a third selection marker wherein said third selection marker is a negative selection marker and wherein said third selection marker is located between the sequences allowing the suppression of the first selection marker. When the vector is circular, the fact that the third selection marker is located between the sequences allowing the suppression of the first selection marker means that the third selection marker and the first selection marker are positioned in the same section of the transfer vector, said section being delimited by the sequences allowing the suppression of the first selection marker.

As used herein, the term "negative selection marker" notably refers to a gene encoding a product that kills the cells that carry the gene under certain conditions. These genes notably comprise "suicide gene". The products encoded by these genes are able to transform a prodrug in a cytotoxic compound. Numerous suicide gene/prodrug pairs are currently available. There may be mentioned more particularly the pairs:

herpes simplex virus type I thymidine kinase (HSV-1 TK) and acyclovir or ganciclovir (GCV) (Caruso et al., 1993, Proc. Natl. Acad. Sci. USA 90, 7024-7028; Culver et al., 1992, Science 256, 1550-1552; Ram et al., 1997, Nat. Med. 3, 1354-1361);

cytochrome p450 and cyclophosphophamide (Wei et al., 1994, Human Gene Therapy 5, 969-978);

purine nucleoside phosphorylase from *Escherichia coli* (*E. coli*) and 6-methylpurine deoxyribonucleoside (Sorscher et al., 1994, Gene Therapy 1, 233-238);

guanine phosphoribosyl transferase from *E. coli* and 6-thioxanthine (Mzoz and Moolten, 1993, Human Gene Therapy 4, 589-595) and cytosine deaminase (CDase) and 5-fluorocytosine (5FC). FCU1 and 5-fluoro-cytosine (5FC) (WO9954481).

FCU1-8 and 5-fluoro-cytosine (5FC) (WO2005007857).

The first, second and third selections marker can be used separately. For example, the vector of the invention can comprise the first and the third selection markers but not the second one, or the second and the third selection markers but not the first one.

According to a preferred embodiment of the invention, the first, the second and/or the third selection marker are placed under the control of the elements necessary for their expression in an host cell.

The elements necessary for the expression consist of the set of elements allowing the transcription of the nucleotide sequence to RNA and the translation of the mRNA to a polypeptide, in particular the promoter sequences and/or regulatory sequences which are effective in said cell, and optionally the sequences required to allow the excretion or the expression at the surface of the host cells for said polypeptide. These elements may be regulatable or constitutive. Of course, the promoter is adapted to the vector selected and to the host cell. There may be mentioned, by way of example, the eukaryotic promoters of the genes PGK (Phospho Glycerate Kinase), MT (metallothionein; McIvor et al., 1987, Mol. Cell. Biol. 7, 838-848), α-1 antitrypsin, CFTR, the promoters of the gene encoding muscle creatine kinase, actin pulmonary surfactant, immunoglobulin or β-actin (Tabin et al., 1982, Mol. Cell. Biol. 2, 416-436), SRα (Takebe et al., 1988, Mol. Cell. 8, 466-472), the SV40 virus (Simian Virus) early promoter, the RSV (Rous Sarcoma Virus) LTR, the MPSV promoter, the TK-HSV-1 promoter, the CMV virus (Cytomegalovirus) early promoter, the vaccinia virus promoters p7.5K pH5R, pK1L, p28, p11 and the adenoviral promoters E1A and MLP or a combination of said promoters. The Cytomegalovirus (CMV) early promoter is most particularly preferred.

The present invention also relates to a cell transfected by a nucleic acid molecule or a vector according to the invention and cells deriving there from. As used herein, the term "derived" refers to cells which develop or differentiate from or have as ancestor a cell transfected by a nucleic acid molecule according to the invention.

The present invention also relates to the use of the polypeptides, nucleotide acid molecules and vectors according to the invention for the immortalization of a cell.

The present invention also relates to a cell comprising the nucleic acid molecule of the invention, wherein said nucleic acid molecule is operably linked to the cell's endogenous HPRT promoter. "Operably linked" is intended to mean that the nucleic acid molecule is linked to the promoter in a manner which allows for its expression in the cell. In a preferred embodiment, the cell according to the invention comprise the nucleic acid sequence set forth in SEQ ID NO:4.

The present invention also relates to a process for immortalizing a cell comprising the step of transfecting a vector according to the invention into said cell.

An immortalized cell, as used herein, refers to a cell capable of growing in culture for more than 35 passages.

The term passage number refers to the number of times that a cell population has been removed from the culture vessel and undergone a subculture (passage) process, in order to keep the cells at a sufficiently low density to stimulate further growth.

As used herein, the term "transfected" refers to the stable transfection or the transient transfection of the cell of the invention.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. The term "transient transfectant" refers to cells that have taken up foreign DNA but have failed to integrate this DNA.

According to a preferred embodiment of the invention, the cell of the invention derives from an avian cell and more preferably from a cell of the Anatidae family or of the Phasianidae family. Among Anatidae, cells belonging to the *Cairina* or *Anas* genus are particularly preferred. Even more preferably, the cells according to the invention belong to the *Cairina moschata* or to the *Anas platyrhynchos* species.

Preferably, the cell according to the invention derives from an embryonic organism. Methods allowing the isolation of cells from a living organism are well known to the one skilled in the art. For example, methods disclosed in example 2 can be used. According to a preferred embodiment of the invention, the primary cell is isolated from an embryo belonging to the Anatidae family which is between 0 and 20 days old, more preferably between 5 and 15 days old and even more preferably between 11 and 14 days old.

When the vector used in the process of the invention comprises a first selection marker. The integration of the first selection marker allows the selection of the cells that have incorporated the nucleic acid molecule of the invention. Accordingly, the process according to the invention can further comprise a step wherein said cells are cultivated in a medium which only allows the growth of the cells which have incorporated the first selection marker. For example in a medium which comprises an antibiotic.

When the vector used in the process of the invention comprises sequences allowing the suppression of the first selection marker, the process according to the invention can further comprise a step consisting in suppressing the first selection marker from the genome of said primary cell. In order to suppress said first selection marker, the cell is transfected by the gene coding the recombinase specific for the sequences allowing the suppression of the first selection marker. Methods and vector able to transfer said gene into the cell are well known to the one skilled in the art, for example, the method disclosed in example 4 of the present application can be used.

When the vector used in the process of the invention comprises a second selection marker, the process according to the invention can further comprise a step wherein the cells are cultivated in a medium which only allows the growth of the cells which have not incorporated the second selection marker. Said step can be made simultaneously with or separately from the step wherein said cells are cultivated in a medium which only allows the growth of the cells which have incorporated the first selection marker.

Said second selection marker is particularly useful when the vector, used in the process according to the invention, is circular. The presence of said second selection marker allows the destruction of the cells in which the homologous recombination process has lead to the introduction of the section of the transfer vector that does not comprise the nucleic acid molecule of the invention.

When the vector used in the process of the invention comprises a third selection marker, the process according to the invention can further comprise a step in which said cell is cultivated in a medium which does not allow the growth of the cells comprising the third selection marker. For example, a medium, which does not allow the growth of the cells comprising FCU1 as a third selection marker, comprises 5-Fluorocytosine.

This step allows the selection of the cells in which the suppression of the first selection marker has occurred. This means that the step consisting in suppressing the first selection marker will also lead to the suppression of the third selection marker. The presence of the third selection marker allows the destruction of the cells in which the first selection marker is present.

The present invention more particularly relates, but is not limited to a process for immortalizing a cell comprising the steps:
of transferring into the cell a vector comprising:
a nucleic acid molecule according to the invention surrounded by homologous sequences.
A first selection marker wherein said first selection marker is a positive selection marker and wherein said first selection marker is surrounded by said homologous sequences.
Sequences allowing the suppression of the first selection marker.
A second selection marker which is not surrounded by said homologous sequences, wherein said selection marker is a negative selection marker.
A third selection marker wherein said third selection marker is a negative selection marker and wherein said third selection marker is located between the sequences allowing the suppression of the first selection marker.
cultivating said cells in a medium which only allows the growth of the cells which have incorporated the first selection marker.
cultivating said cells in a medium which does not allow the growth of the cells which have incorporated the second selection marker.
excluding the first selection marker from the genome of said cell.
cultivating said cell in a medium which does not allow the growth of the cells comprising the third selection marker.

In a particularly preferred embodiment, the invention relates to an immortalized cell which derives from a cell of an animal belonging to the *Cairina moschata* species and which comprises the *Cairina moschata* telomerase reverse transcriptase, under the control of the *Cairina moschata* HPRT promoter, inserted into the HPRT gene of the cell.

The cell according to the invention can further comprise one or more nucleic acid sequence allowing the propagation of a defective virus. "Defective virus" refers to a virus in which one or more viral gene necessary for its replication are deleted or rendered nonfunctional. The term "nucleic acid sequence allowing the propagation of a defective virus" refers to a nucleic acid sequence supplying in trans the function(s) which allows the replication of the defective virus. In other words, said nucleic acid sequence(s) codes the proteins(s) necessary for the replication and encapsidation of said defective virus. By way of illustration, for the production of an adenoviral vector, lacking most of the E1 region, the cell according to the invention can be transfected transiently or permanently with a nucleic acid sequence coding the E1 region.

The cell according to the invention can also comprise a nucleic acid sequence coding a substance of interest. As used herein, a substance of interest may include, but is not limited to, a pharmaceutically active protein, for example growth factors, growth regulators, antibodies, antigens, their derivatives useful for immunization or vaccination and the like, interleukins, insulin, G-CSF, GM-CSF, hPG-CSF, M-CSF or combinations thereof, interferons, for example, interferon-α, interferon-β, interferon-, blood clotting factors, for example, Factor VIII, Factor IX, or tPA or combinations thereof. "Substance of interest" also refers to industrial enzymes, for example for use within pulp and paper, textile modification, or ethanol production. Finally, "substance of interest" also refers to protein supplement or a value-added product for animal feed.

The cells obtained by the process according to the invention, the cell of the invention and the cells derived thereof are notably useful for the replication of a virus. Said viruses can be live, attenuated, recombinant or not. More preferably, said cells are particularly useful for the replication of poxvirus (vaccinia virus, in particular MVA, canarypoxvirus, etc.), an adenovirus, a retrovirus, an herpesvirus, an alphavirus, a foamy virus or from an adenovirus-associated virus.

Retroviruses have the property of infecting, and in most cases integrating into, dividing cells and in this regard are particularly appropriate for use in relation to cancer. A recombinant retrovirus according to the invention generally contains the LTR sequences, an encapsidation region and the nucleotide sequence according to the invention, which is placed under the control of the retroviral LTR or of an internal promoter such as those described below. A retroviral vector may contain modifications, in particular in the LTRs (replacement of the promoter region with a eukaryotic promoter) or the encapsidation region (replacement with a heterologous encapsidation region, for example the VL30 type) (see French applications 94 08300 and 97 05203).

Adenoviral vector can lacks all or part of at least one region which is essential for replication and which is selected from the E1, E2, E4 and L1 L5 regions. A deletion of the E1 region is preferred. However, it can be combined with (an)other modification(s)/deletion(s) affecting, in particular, all or part of the E2, E4 and/or L1 L5 regions. By way of illustration, deletion of the major part of the E1 region and of the E4 transcription unit is very particularly advantageous. For the purpose of increasing the cloning capacities, the adenoviral vector can additionally lack all or part of the non-essential E3 region. According to another alternative, it is possible to make use of a minimal adenoviral vector which retains the sequences which are essential for encapsidation, namely the 5' and 3' ITRs (Inverted Terminal Repeat), and the encapsidation region. The various adenoviral vectors, and the techniques for preparing them, are known (see, for example, Graham and Prevect, 1991, in Methods in Molecular Biology, Vol 7, p 109 128; Ed: E. J. Murey, The Human Press Inc).

Poxvirus family comprises viruses of the Chordopoxvirus and Entomopoxvirus subfamilies. Among these, the poxvirus according to the invention is preferably chosen from the group comprising Orthopoxviruses, Parapoxviruses, Avipoxviruses, Capripoxviruses, Leporipoxviruses, Suipoxviruses, Molluscipoxviruses, Yatapoxviruses. According to a more preferred embodiment, the poxvirus of the invention is an orthopoxvirus.

The Orthopoxvirus is preferably a vaccinia virus and more preferably a modified vaccinia virus Ankara (MVA) in particular MVA 575 (ECACC V00120707) and MVA-BN (ECACC V00083008).

The term "recombinant virus" refers to a virus comprising an exogenous sequence inserted in its genome. As used herein, an exogenous sequence refers to a nucleic acid which is not naturally present in the parent virus.

In one embodiment, the exogenous sequence encodes a molecule having a directly or indirectly cytotoxic function. By "directly or indirectly" cytotoxic, we mean that the molecule encoded by the exogenous sequence may itself be toxic (for example ricin, tumour necrosis factor, interleukin-2, interferon-gamma, ribonuclease, deoxyribonuclease, *Pseudomonas* exotoxin A) or it may be metabolised to form a toxic product, or it may act on something else to form a toxic product. The sequence of ricin cDNA is disclosed in Lamb et al (Eur. J. Biochem., 1985, 148, 265-270) incorporated herein by reference.

In a preferred embodiment of the invention, the exogenous sequence is a suicide gene. A suicide gene encodes a protein able to convert a relatively non-toxic prodrug to a toxic drug. For example, the enzyme cytosine deaminase converts 5-fluorocytosine (5FC) to 5-fluorouracil (5FU) (Mullen et al (1922) PNAS 89, 33); the herpes simplex enzyme thymidine kinase sensitises cells to treatment with the antiviral agent ganciclovir (GCV) or acyclovir (Moolten (1986) Cancer Res. 46, 5276; Ezzedine et al (1991) New Biol 3, 608). The cytosine deaminase of any organism, for example *E. coli* or *Saccharomyces cerevisiae*, may be used.

Thus, in a more preferred embodiment of the invention, the gene encodes a protein having a cytosine deaminase activity and even more preferably a protein as described in patent applications WO2005007857 and WO9954481.

In a further embodiment the exogenous gene encodes a ribozyme capable of cleaving targeted RNA or DNA. The targeted RNA or DNA to be cleaved may be RNA or DNA which is essential to the function of the cell and cleavage thereof results in cell death or the RNA or DNA to be cleaved may be RNA or DNA which encodes an undesirable protein, for example an oncogene product, and cleavage of this RNA or DNA may prevent the cell from becoming cancerous.

In a still further embodiment the exogenous gene encodes an antisense RNA.

By "antisense RNA" we mean an RNA molecule which hybridises to, and interferes with the expression from a mRNA molecule encoding a protein or to another RNA molecule within the cell such as pre-mRNA or tRNA or rRNA, or hybridises to, and interferes with the expression from a gene.

In another embodiment of the invention, the exogenous sequence replaces the function of a defective gene in a target cell. There are several thousand inherited genetic diseases of mammals, including humans, which are caused by defective genes. Examples of such genetic diseases include cystic fibrosis, where there is known to be a mutation in the CFTR gene; Duchenne muscular dystrophy, where there is known to be a mutation in the dystrophin gene; sickle cell disease, where there is known to be a mutation in the HbA gene. Many types of cancer are caused by defective genes, especially protooncogenes, and tumour-suppressor genes that have undergone mutation.

Examples of protooncogenes are ras, src, bcl and so on; examples of tumour-suppressor genes are p53 and Rb.

In a further embodiment of the invention, the exogenous sequence encodes a Tumor Associated Antigen (TAA). TAA refers to a molecule that is detected at a higher frequency or density in tumor cells than in non-tumor cells of the same tissue type. Examples of TAA includes but are not limited to CEA, MART-1, MAGE-1, MAGE-3, GP-100, MUC-1, MUC-2, pointed mutated ras oncogene, normal or point mutated p53, overexpressed p53, CA-125, PSA, C-erb/B2, BRCA I, BRCA II, PSMA, tyrosinase, TRP-1, TRP-2, NY-ESO-1, TAG72, KSA, HER-2/neu, bcr-abl, pax3-fkhr, ews-fli-1, surviving and LRP. According to a more preferred embodiment the TAA is MUC1.

The recombinant virus can comprise more than one exogenous sequence and each exogenous sequence can encodes more than one molecule. For example, it can be useful to associate in a same recombinant poxvirus, an exogenous sequenced coding a TAA with an exogenous sequence coding a cytokine.

In another embodiment of the invention, the exogenous gene encodes an antigen. As used herein, "antigen" refers to a ligand that can be bound by an antibody; an antigen need not itself be immunogenic.

Preferably the antigen is derived from a virus such as for example HIV-1, (such as gp 120 or gp 160), any of Feline Immunodeficiency virus, human or animal herpes viruses, such as gD or derivatives thereof or Immediate Early protein such as ICP27 from HSV1 or HSV2, cytomegalovirus (such as gB or derivatives thereof), Varicella Zoster Virus (such as gpI, II or III), or from a hepatitis virus such as hepatitis B virus for example Hepatitis B Surface antigen or a derivative thereof, hepatitis A virus, hepatitis C virus (preferentially non structural protein from genotype 1b strain ja) and hepatitis E virus, or from other viral pathogens, such as Respiratory Syncytial Virus, Human Papilloma Virus (preferentially the E6 and E7 protein from the HPV16 strain) or Influenza virus, or derived from bacterial pathogens such as *Salmonella, Neisseria, Borrelia* (for example OspA or OspB or derivatives thereof), or *Chlamydia*, or *Bordetella* for example P.69, PT and FHA, or derived from parasites such as *plasmodium* or *Toxoplasma*.

FIG. 1: Vector comprising a gene coding the telomerase reverse transcriptase.

Figure 2:
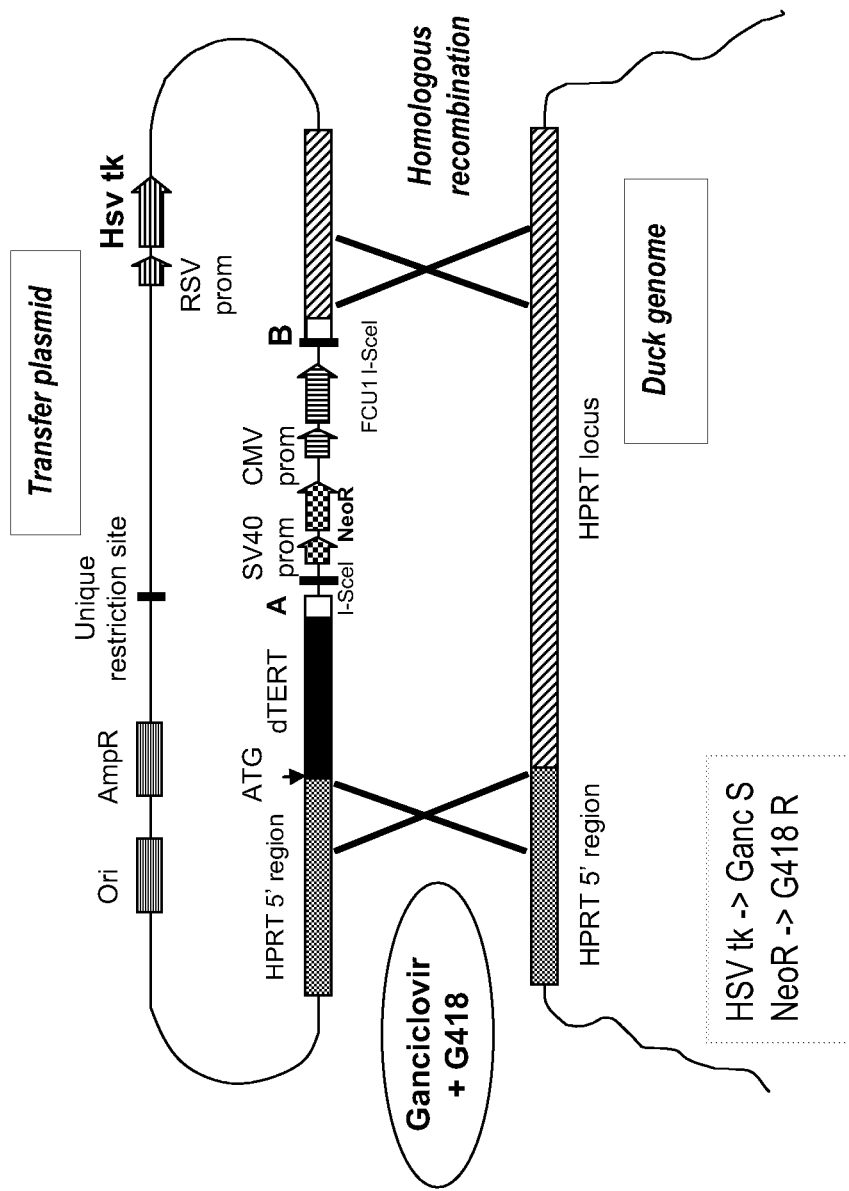

FIG. 2: Schematic representation of the site specific insertion of the gene coding the telomerase reverse transcriptase into the HPRT gene.

Figure 3:
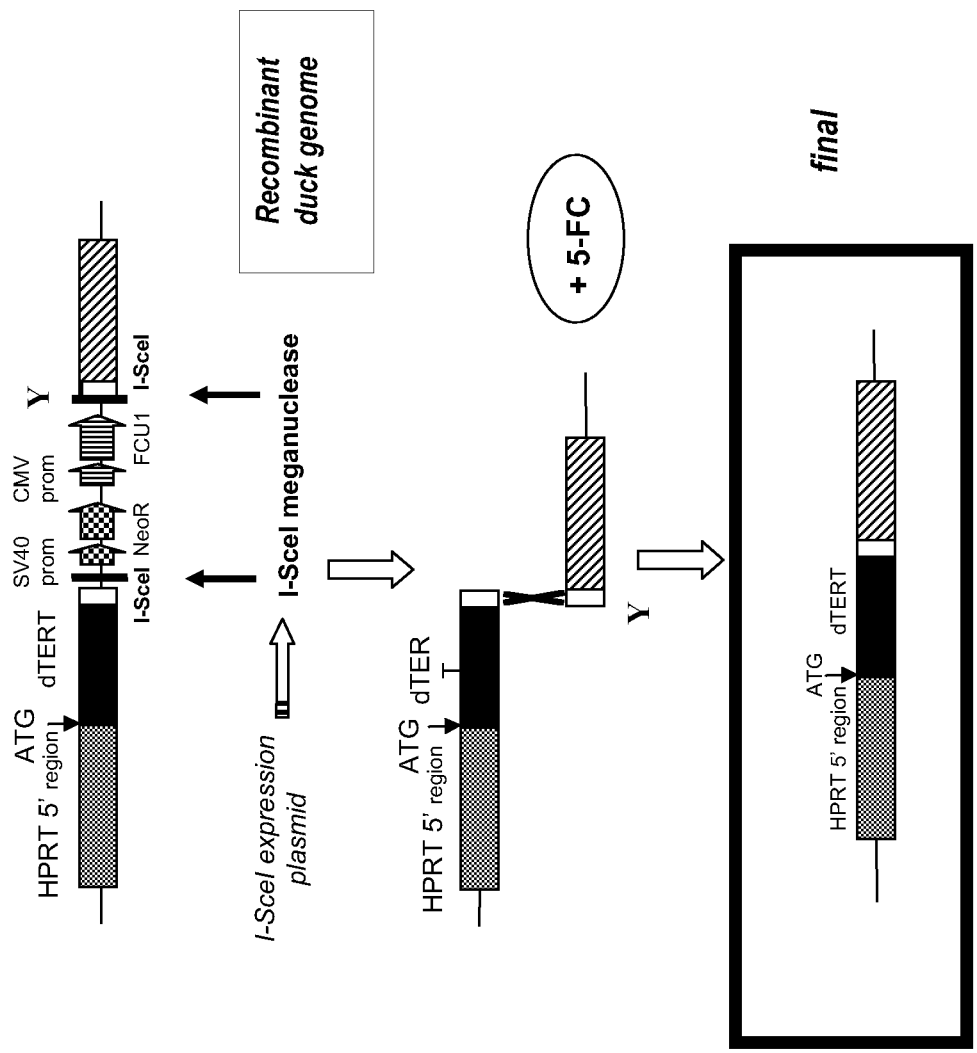

FIG. 3: Schematic representation of the elimination of the first and the third selection marker from the genome of the immortalized cell obtained by the process of the invention.

EXAMPLES

Example 1

Telomerase Expression System

Random Insertion

A plasmid sharing no specific sequence of homology with the duck genome has been used for this purpose (FIG. 1).

Targeted Insertion

A plasmid comprising two 5 kb fragments homologous to the *Cairina moschata* HPRT gene surrounding the *cairina moschata* telomerase reverse transcriptase gene and two selection markers has been constructed. The HPRT gene encoding for the hypoxanthine guanine phosphoryl transferase has been selected as an adequate site for the constitutive expression of the *cairina moschata* telomerase.

These two selection marker are the FCU1 gene (Erbs et al. Cancer Res. 2000. 15. 60.:3813-22) under the control of a CMV promoter (Thomsen et al. P.N.A.S. 1984. 81. 3:659-63) and the Neomycin resistance gene placed under the control of a SV40 promoter. Neomycin resistance and FCU-1 expression cassette are surrounded by Sce1 cleavage sites that allow the elimination of the selection cassettes from the final cell line. Outside of the HPRT gene arms is inserted a selection marker coding the HSVTK driven by an RSV promoter (FIG. 2).

Example 2

Preparation of CEC Batch from 12 Old *Cairina moschata* Eggs and Subpopulations Description 25 fertilized SPF eggs are incubated at 37.5° C. Eggs are opened after 12 days incubation following available protocol.

23 embryos are minced, washed once in Phosphate Buffered Saline-Dulbecco (PBS) and dissociated in TrypLE Select (Invitrogen) 5 hours at room temperature.

After low speed centrifugation cells are resuspended in Basal Medium Eagle (MBE) supplemented with 10% fetal calf serum (FCS), gentamycin 0.04 g/L, seeded in 500 cm² triple flasks and incubated at 37° C. 5% $CO_2$.

After 24 h the confluent cells are removed from the flasks using TrypLE Select (5 mL/triple flask), part of the cells were reseeded in 175 cm² flasks for second passage. The remaining cells were concentrated at $10^7$ cell/mL in appropriate media (60% BME, 30% FCS and 10% DMSO) and frozen in a isopropyl alcohol regulated container (NALGENE.®. "Mr. Frosty" 1° C. freezing. Container) at −80° C. prior to transfer in liquid azote for long term storage, constituting the initial cell bank ($50 \times 1.5 \cdot 10^7$ cells/vial, $44 \times 1 \cdot 10^7$ cells/vial).

Cells remained in culture are passaged classically up to 18 passages, during the 3 first passages non attached cells are collected by low centrifuging the conditioned media, reseeded and further passaged in the same way as the initial culture.

Subpopulations, displaying characteristic different morphological features, have been reproducibly isolated during the culture's lifespan.

Example 3

Methods of Transfection

A large number of transfection methods are known in the art to introduce a vector capable of directing expression of a nucleotide sequence of interest. A non limiting list of these methods is listed hereafter: $CaPO_4$ precipitation, electroporation, lipofectin transfection method. A given example is based on $CaPO_4$ precipitation procedure.

Cells should be around 80-50% confluency. The medium is change two hours before $CaPO_4$/DNA addition. The 30 μg DNA is resuspended in 31 μl 2M $CaCl_2$-161.3 mM Tris pH 7.6. $H_2O$ is added to a final volume of 0.5 ml.

Per transfection, 0.5 ml of 2×HEBS is distributed in 15 ml sterile Falcon tube and the DNA solution is added drop wise while gently vortexing or bubbling the DNA solution in. The solution should become milky. The mix is let stand at room temperature for 10-30 min. Then pipette in and out once with sterile pipette in tissue culture cabinet to break up flakes and apply drop wise to cells. Cells are then incubated between 6 hours to overnight at 37° C. A fine precipitate should cover the cell surface. In order to complete the transfection procedure warm up to 37° C. the glycerol shock solution. The medium is aspirate off, 5 ml BME is added to wash the cell layer, the medium is then aspirate off and 1 ml glycerol shock solution is added for 2 min or less. Subsequently 10 ml BME are added gently to dilute the glycerol and BME-glycerol is completely removed. 10 ml of desired medium is then added and plates are incubated at the appropriate temperature.

Example 4

Methods of Selection

Random Insertion:

Selection pressure is applied 48 hours after transfection: cells are dissociated with TrypLE select, low speed centrifuged and reseeded in BME with FCS 10%, and G418 800 μg/mL.

Cells are serially passaged until individual growing clones can be isolated. The multiplying foci are isolated and amplified prior to telomerase activity quantification with TRA-Peze® XL telomerase detection kit (S7707, Chemicon) and southern blot analysis to establish the integration in the targeted specific locus.

Targeted Insertion:

Selection pressure is applied 48 hours after transfection: cells are dissociated with TrypLE select, low speed centrifuged and reseeded in BME with FCS 10%, Ganciclovir 25 μg/mL, and G418 800 μg/mL.

Cells are serially passaged until individual growing clones can be isolated. The multiplying foci are isolated and amplified prior to telomerase activity quantification with TRA-Peze® XL telomerase detection kit (S7707, Chemicon) and southern blot analysis oligos to establish the integration in the targeted specific locus.

Cell clones with detected restored telomerase activity and targeted HPRT locus integration are subsequently transfected with a meganuclease I-SceI expression plasmid following the method described below.

To select the elimination of the selection markers 5-Fluorocytosine (5-FC) is applied 48 hours after transfection: cells are dissociated with TrypLE select, low speed centrifuged and reseeded in media with 5-FC concentration ranging from $10^{-3}$ to $10^{-7}$ M and maintained G418 selection (BME with FCS 10%, 5-FC, and G418 800 μg/mL).

The invention claimed is:

1. A recombinant cDNA nucleic acid molecule comprising the nucleotide sequence as set forth in SEQ ID NO: 2, wherein expression of said nucleic acid molecule in an isolated avian cell exhibits telomerase reverse transcriptase (TERT) activity.

2. A vector comprising the nucleic acid molecule of claim 1.

3. The vector of claim 2, wherein said vector comprises two sequences homologous to a target DNA sequence.

4. The vector of claim 3, wherein said nucleic acid molecule is surrounded by said homologous sequences.

5. The vector of claim 3, wherein said vector further comprises a first selection marker wherein said first selection marker is a positive selection marker and wherein said first selection marker is surrounded by said homologous sequences.

6. The vector of claim 5, wherein said first selection marker is surrounded by sequences allowing its suppression.

7. The vector of claim 3, wherein said vector comprises a second selection marker which is not surrounded by said homologous sequences and wherein said selection marker is a negative selection marker.

8. The vector of claim 6, wherein said vector comprises a third selection marker wherein said third selection marker is a negative selection marker and wherein said third selection marker is located between the sequences allowing the suppression of the first selection marker.

9. An isolated avian cell comprising the nucleic acid molecule of claim 1.

10. The isolated avian cell of claim 9, wherein said nucleic acid molecule is inserted into the Hypoxanthine phosphorylbosyl transferase (HPRT) gene of said avian cell.

11. The isolated avian cell of claim 9, wherein said isolated avian cell is from an animal belonging to the Anatidae family.

12. The isolated avian cell of claim 11, wherein said animal belongs to the *Cairina moschata* species.

13. The isolated avian cell of claim 11, wherein said animal belongs to the *Anas platyrhynchos* species.

14. The isolated avian cell of claim 9, wherein it further comprises a nucleic acid sequence coding a protein of interest.

15. The isolated avian cell of claim 9, wherein it further comprises a complementation cassette allowing the propagation of a defective virus.

* * * * *